United States Patent
Martin et al.

(10) Patent No.: US 10,718,778 B2
(45) Date of Patent: Jul. 21, 2020

(54) COMPOSITIONS AND METHODS FOR DETECTING PROTEIN SULFENYLATION

(71) Applicant: THE REGENTS OF THE UNIVERSITY OF MICHIGAN, Ann Arbor, MI (US)

(72) Inventors: Brent R. Martin, Ann Arbor, MI (US); Christopher Baker Tom, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/313,445

(22) PCT Filed: May 29, 2015

(86) PCT No.: PCT/US2015/033217
§ 371 (c)(1),
(2) Date: Nov. 22, 2016

(87) PCT Pub. No.: WO2015/184281
PCT Pub. Date: Dec. 3, 2015

(65) Prior Publication Data
US 2017/0192010 A1 Jul. 6, 2017

Related U.S. Application Data

(60) Provisional application No. 62/005,238, filed on May 30, 2014.

(51) Int. Cl.
| | | |
|---|---|---|
| *A61K 49/00* | (2006.01) | |
| *G01N 33/68* | (2006.01) | |
| *C12P 21/00* | (2006.01) | |
| *A61K 49/10* | (2006.01) | |

(52) U.S. Cl.
CPC ..... *G01N 33/6815* (2013.01); *A61K 49/0052* (2013.01); *A61K 49/10* (2013.01); *C12P 21/00* (2013.01); *G01N 33/6848* (2013.01); *G01N 2440/00* (2013.01); *G01N 2458/15* (2013.01); *G01N 2560/00* (2013.01)

(58) Field of Classification Search
CPC .... A61K 49/00; A61K 49/10; A61K 49/0052; A61K 51/00; G01N 33/6815; G01N 33/6848; G01N 2560/00; G01N 2458/15; G01N 2440/00; C12P 21/00
USPC .......... 424/1.11, 1.49, 1.65, 1.69, 1.81, 1.85, 424/1.89, 9.1, 9.2, 9.3, 9.6
See application file for complete search history.

(56) References Cited

U.S. PATENT DOCUMENTS

2006/0084173 A1  4/2006  Poole et al.
2014/0147905 A1  5/2014  Benkovic et al.

OTHER PUBLICATIONS

Allison, W. S., "Formation and Reactions of Sulfenic Acids in Proteins" 1976 Accounts of Chemical Research 9, 293-299.
Bonifati, V. et al., "Mutations in the DJ-1 gene associated with autosomal recessive early-onset parkinsonism." 2003 Science 299, 256-259.
Crump, K. E., et al. "The reversible formation of cysteine sulfenic acid promotes B-cell activation and proliferation" 2009 European Journal of Immunology 42, 2152-2164.
Fuchigami, T., et al., "Electrolytic Partial Fluorination of Organic Compounds . . . " 1995 Journal of Organic Chemistry 60, 3459-3464.
Gautier, V. et al., "YajL, the Prokaryotic Homolog of the Parkinsonism-Associated Protein DJ-1, Protects Cells against Protein Sulfenylation" 2012 Journal of Molecular Biology 421, 662-670.
Higuchi, M. et al., "19F and 1H MRI detection of amyloid B plaques in vivo" 2005 Nature Neuroscience 8, 527-533.
International Search Report and Written Opinion, Int'l Patent Application No. PCT/US2015/033217, dated Nov. 9, 2015.
Kitamura, N., et al., "Heat-initiated detection for reduced glutathione with 19F NMR probes based on modified gold nanoparticles" 2013 Bioorganic & Medicinal Chemistry Letters 23, 281-286.
Klomsiri, C., et al., "Cysteine-Based Redox Switches in Enzymes" Antioxidants & Redox Signaling 14, 1065-1077 (2011).
Knight, J. C., et al., "Fluorinated contrast agents for magnetic resonance imaging; a review of recent developments" 2011 Rsc Advances 1, 1415-1425.
Lavis, L. D. & Raines, R. T., "Bright Ideas for Chemical Biology" 2008 Acs Chemical Biology 3, 142-155.
Leonard, S. E., et al., "Mining the Thiol Proteome for Sulfenic Acid Modifications Reveals New Targets for Oxidation in Cells" 2009 Acs Chemical Biology 4, 783-799.
Lopachin et al. "β-Dicarbonyl Enolates: A New Class of Neuroprotectants" J. Neurochem 116(1): 132-143, 2011.
Paulsen, C. E & Carroll, K. S. "Cysteine-Mediated Redoc Signaling: Chemistry, Biology, and Tools for Discovery" 2013 Chemical Reviews 113, 4633-4679.
Poole, L. B., et al., "Synthesis of Chemical Probes to Map Sulfenic Acid Modifications on Proteins" 2005 Bioconjugate Chemistry 16, 1624-1628.
Pubchem, Compound Summary for SID 119536780, Create Date: May 5, 2011 [retreived on Jul. 31, 2015].

(Continued)

*Primary Examiner* — D. L. Jones
(74) *Attorney, Agent, or Firm* — Casimir Jones, SC; Robert A. Goetz

(57) ABSTRACT

The present invention relates to methods for detecting sulfenylation within thiol groups in proteins, metabolites, or materials. Protein sulfenylation (Cys-SOH) describes the reversible post-translational modification of protein thiols by hydrogen peroxide, and plays a central role in oxidative signaling (see, e.g., Paulsen, C. E. & Carroll, K. S. 2013 Chemical Reviews 113, 4633-679). Growth factor stimulation activates NADPH oxidase enzymes, releasing a local burst of hydrogen peroxide, which transiently oxidizes the nucleophilic cysteine of protein phosphatases and other proximal redox active thiols (see, e.g., Paulsen, C. E. et al., 2012 Nature Chemical Biology 8, 57-64). In addition to masking functional cysteine's, sulfenylation is also a critical intermediate towards irreversible cysteine oxidation.

15 Claims, 16 Drawing Sheets

(56) References Cited

OTHER PUBLICATIONS

Qian, J. et al., "Simple synthesis of 1,3-cyclopentanedione derived probes for labeling sulfenic acid proteins" 2011 Chemical Communications 47, 9203-9205.

Qian, J. et al., "A simple and effective strategy for labeling cysteine sulfenic acid in proteins . . . " 2012 Chemical Communications 48, 4091-4093.

Saleur, D., et al., "Bis(acylsilanes) and Trifluoromethyltrimethylsilane: A useful system for the synthesis . . . " 2001 Journal of Organic Chemistry 66, 4543-4548.

Schwarz, R., et al., "19F-MRI of Perfluorononane as a Novel Contrast Modality for Gastrointestinal Imaging" 1999 Magnetic Resonance in Medicine 41, 80-86.

Seo, Y. H. & Carroll, K S. "Profiling protein thiol oxidation in tumor cells using sulfenic acid-specific antibodies" 2009 Proc Natl Acad Sci U S A 106, 16163-16168.

Tanner, J. J., et al., "Redox Regulation of Protein Tyrosine Phosphatases: Structural and Chemical Aspects" 2011 Antioxidants & Redox Signaling 15, 77-97.

Yamaguchi, K. et al., 2011 "Design of Chemical Shift-Switching 19F Magnetic Resonance Imaging Probe for Specific Detection of Human Monoamine Oxidase A" Journal of the American Chemical Society 133, 14208-14211.

Direct electronic pertubation (DiNap mechanism)

Cyanine

Indirect electronic purturbation (via PET)

BODIPY

Fluorophore release (chemical reactivity switch)

X = N, C-Aryl

Fluorscein, resorufin a b a b c d wildtype/control       disease/stimulus

COMPOSITIONS AND METHODS FOR DETECTING PROTEIN SULFENYLATION

FIELD OF THE INVENTION

The present invention relates to methods for detecting sulfenylation within thiol groups in proteins, metabolites, or materials.

BACKGROUND OF THE INVENTION

Improved methods for detecting protein sulfenylation are needed.

SUMMARY OF THE INVENTION

Protein sulfenylation (Cys-SOH) describes the reversible post-translational modification of protein thiols by hydrogen peroxide, and plays a central role in oxidative signaling (see, e.g., Paulsen, C. E. & Carroll, K. S. 2013 Chemical Reviews 113, 4633-4679). Growth factor stimulation activates NADPH oxidase enzymes, releasing a local burst of hydrogen peroxide, which transiently oxidizes the nucleophilic cysteine of protein phosphatases and other proximal redox active thiols (see, e.g., Paulsen, C. E. et al., 2012 Nature Chemical Biology 8, 57-64). In addition to masking functional cysteines, sulfenylation is also a critical intermediate towards irreversible cysteine oxidation. Recent chemical proteomic strategies take advantage of the sulfenic acid-reactive active methylene compound (AMC) dimedone (5,5-dimethylcyclohexane-1,3-dione) (see, e.g., Paulsen, C. E. & Carroll, K. S. 2013 Chemical Reviews 113, 4633-4679; Leonard, S. E., et al., Acs Chemical Biology 4, 783-799; Seo, Y. H. & Carroll, K. S. 2009 Proc Natl Acad Sci USA 106, 16163-16168). This small molecule acts as a covalent trap, reacting with sulfenic acids to form a stable and irreversible thioether linkage. Dimedone-conjugates (see, e.g., Leonard, S. E., et al., 2009 Acs Chemical Biology 4, 783-799; Poole, L. B., et al., Bioconjugate Chemistry 16, 1624-1628) and dimedone-specific monoclonal antibodies (see, e.g., Seo, Y. H. & Carroll, K. S. 2009 Proc Natl Acad Sci USA 106, 16163-16168) have been used in biochemical and proteomics studies to highlight the widespread targets of sulfenylation, including the characterization of novel redox signaling pathways in EGFR (see, e.g., Paulsen, C. E. et al., 2012 Nature Chemical Biology 8, 57-64) and B-cell activation (see, e.g., Crump, K. E., 2009 European Journal of Immunology 42, 2152-2164). These studies suggest an underappreciated functional role for this widespread oxidative post-translational modification in many aspects of signaling and disease (see, e.g., Paulsen, C. E. & Carroll, K. S. 2013 Chemical Reviews 113, 4633-4679).

While these tools are useful for biochemical and proteomics assays, little is known about the sub-cellular dynamics of protein sulfenylation. Current methods to image sulfenylation require labeling with dimedone analogues, followed by harsh fixation and washing steps (see, e.g., Paulsen, C. E. et al., 2012 Nature Chemical Biology 8, 57-64; Seo, Y. H. & Carroll, K. S. 2009 Proceedings of the National Academy of Sciences of the United States of America 106, 16163-16168). While these approaches yield fluorescence images on fixed cells, it is impossible to assign whether these methods label conjugated or unbound probe. Furthermore, there are no current methods for live-cell imaging of protein sulfenylation, which is a major impediment to the study of protein oxidation.

The present invention provides new methods to visualize the role of protein sulfenylation in vivo, and apply such methods to characterize the functional significance of this modification in disease. In addition, the present invention provides mechanism-based chemical probes to analyze the spatiotemporal dynamics in cells and as a platform to image biological sulfenylation in vivo.

Indeed, experiments conducted during the course of developing embodiments for the present invention developed a chemoselective 'switch' to introduce a new generation of probes for detecting protein sulfenylation. Dimedone ($pK_a$=4.3) is predominantly in the enolate form under physiological conditions, leaving a single proton linked to the α-carbon. Once dimedone reacts and forms a thioether bond, the reactive carbon returns to the enolate form, displacing the remaining proton. The present invention provides dimedone based probes wherein the single α-proton is replaced by fluorine, thereby locking the reacted probe as the di-ketone, which changes the electronics of the conjugated fluorophore. As such, the present invention provides small molecule covalent probes capable of ratiometric fluorescence imaging of a post-translational modification in live cells. Furthermore, conjugation results in a dramatic change in the fluorine electronic environment at the reactive α-carbon. This reconfiguration results in a robust $^{19}$F-NMR change, extending detection beyond single cells.

Accordingly, in certain embodiments, the present invention provides methods for detecting protein sulfenylation within cysteine residues of a protein, comprising providing a biological sample comprising one or more proteins having cysteine residues and a composition comprising a probe having a chemical moiety configured to switch from an enolate form to a di-ketone form upon conjugation with a sulfenic acid side chain of a cysteine residue. Such methods further involve exposing the composition to the biological sample such that an interaction between the probe and a sulfenic acid side chain of a cysteine residue results in conjugation of the probe with the sulfenic acid side chain, measuring the spectroscopic properties of the probe following exposure of the composition to the biological sample, wherein and characterizing the cysteine residues of the protein as having undergone sulfenylation if the measuring indicates the presence of the probe in a di-ketone form. In some embodiments, the methods further involve identifying the protein having been characterized as having undergone sulfenylation and/or identifying the exact amino acid sites on the protein having been characterized as having undergone sulfenylation.

Such methods are not limited to use of a particular probe. In some embodiments, the probe is selected from the group consisting of

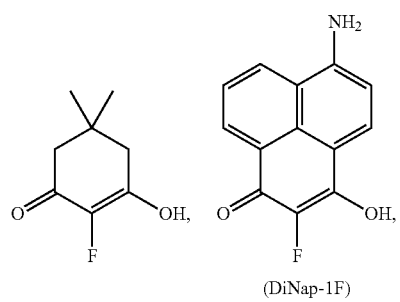

(DiNap-1F)

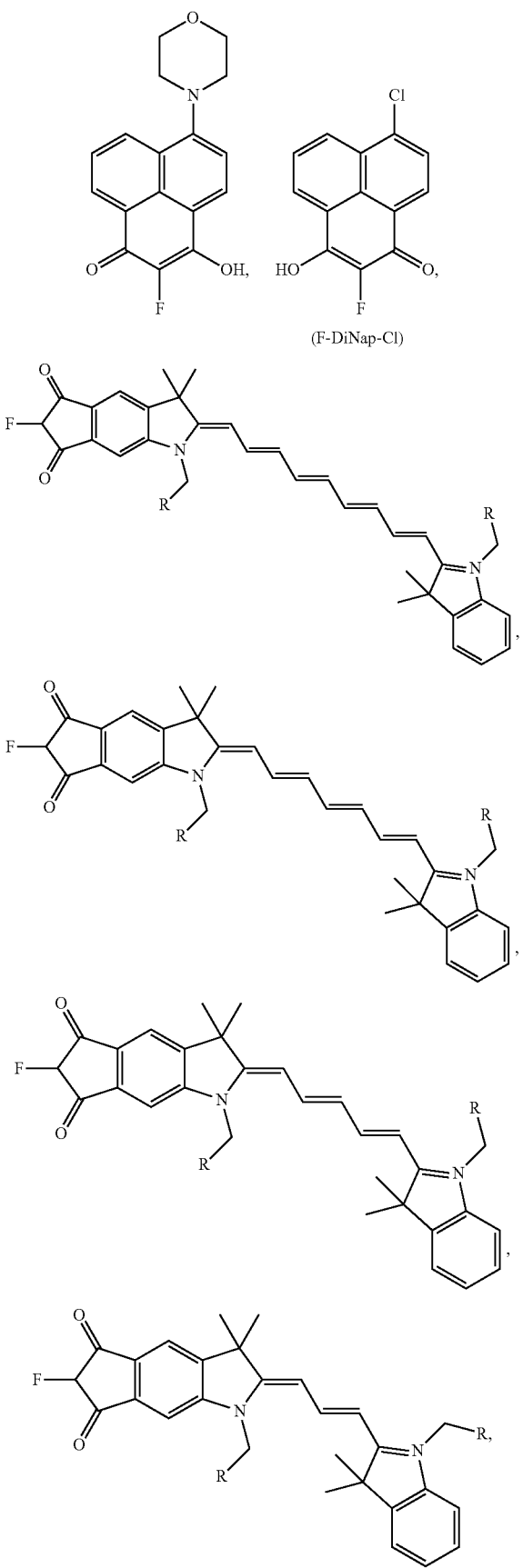
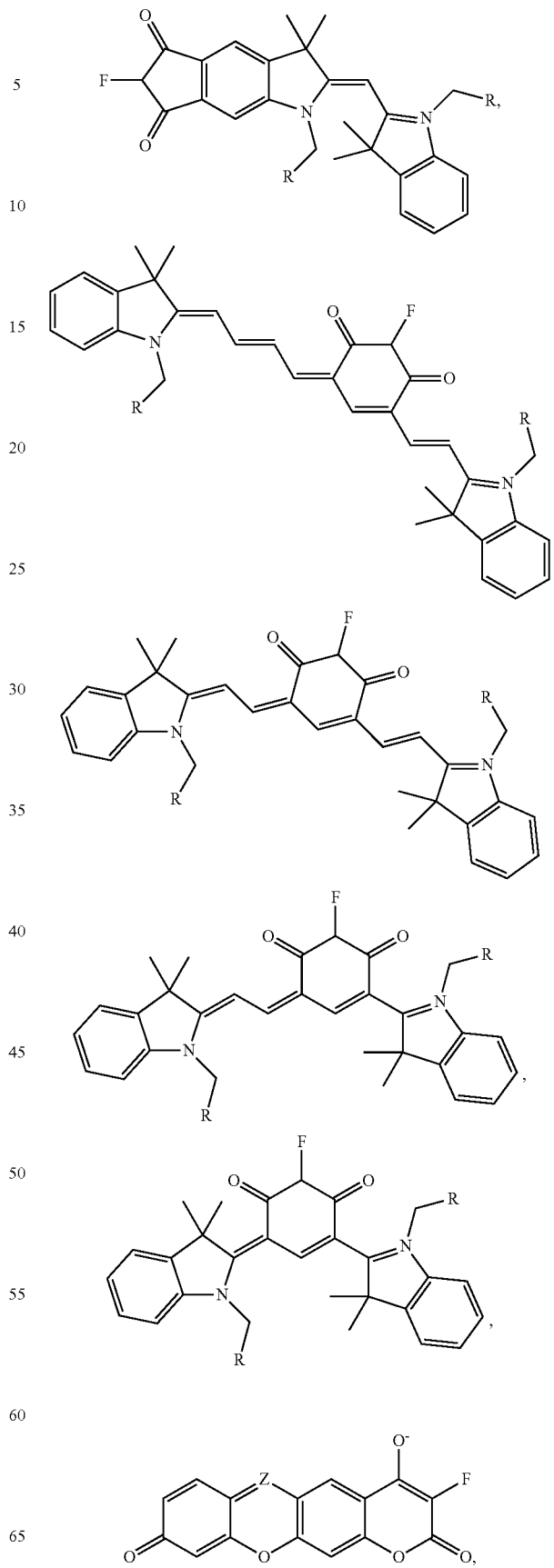

-continued

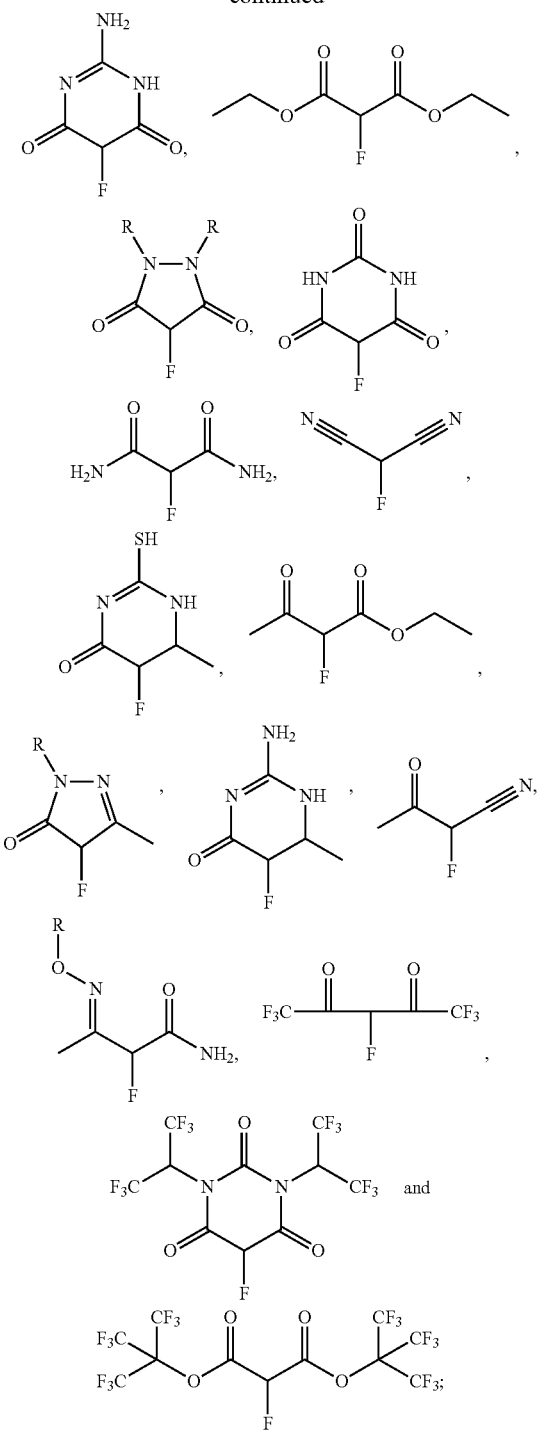

wherein Z is N or C-aryl; wherein R is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms), or a water-solubilizing group (sulfate, amine, carboxylic acid or other charged or polar functional handle).

In some embodiments, the probe is

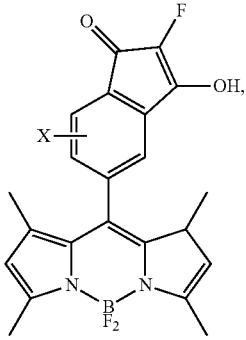

wherein X is either an electron-withdrawing chemical moiety or an electron donating chemical moiety. For example, in some embodiments wherein X is an electron-withdrawing chemical moiety, X is selected from C(O)H, C(O)$R_1$, C(O)OH, C(O)O$R_1$, C(O)$R_2$, C($R_2$)3, CN, S(O)$_2$OH, $NH_3^+$, C(O)N(R)$_2$, N(R)$_3^+$, and $NO_2$; and wherein $R_1$ is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms); and wherein $R_2$ is a halogen (e.g., Cl, F, I). For example, in some embodiments wherein X is an electron-donating chemical moiety, X is selected from Oxygen, N($R_1$)$_2$, $NH_2$, SH, $SR_1$, OH, $OR_1$, NHC(O)$R_1$, $R_1$, benzene, C(H)=C($R_2$)$_2$; and wherein $R_1$ is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms).

In some embodiments, the probe is shown in FIGS. 8, 10 and/or 11.

Such methods are not limited to a particular manner of measuring the spectroscopic properties of the probe. In some embodiments, the spectroscopic properties are measured with ratiometric fluorescence imaging. In some embodiments, the spectroscopic properties are measured with $^{19}$F-NMR/MRI. In some embodiments, the spectroscopic properties are measured with $^1$H-NMR/MRI. In some embodiments, the probe is synthesized with a $^{13}$C labeled α-carbon, and the spectroscopic properties will be measured with $^{13}$C-NMR/MRI.

Such methods are not limited to a particular type of biological sample. In some embodiments, the biological sample is an ex vivo sample obtained from a living subject. In some embodiments, the biological sample is an in vitro biological sample. In some embodiments, the biological sample is a living mammalian subject (e.g., a living human being, a living mouse, etc.).

In some embodiments, mass spectrometry is used to characterize the cysteine residues of the protein characterized as having undergone protein sulfenylation.

In certain embodiments, the present invention provides methods of identifying pharmaceutical agents capable of inhibiting protein sulfenylation, comprising providing a pharmaceutical agent and a biological sample comprising one or more proteins having cysteine residues known to undergo sulfenylation, exposing the pharmaceutical agent to the biological sample, characterizing the cysteine residues of the one or more proteins as having or not having undergone sulfenylation with the described methods for detecting protein sulfenylation, and identifying the pharmaceutical agent as a sulfenylation inhibitor if the characterizing indicates an absence of sulfenylation.

In some embodiments, antibodies specific for proteins characterized as having undergone protein sulfenylation are provided. For example, in some embodiments, antibodies specific to this modification are developed and used for selective enrichment. In some embodiments, such a modification is specific to the tetrahedral α-carbon. In some embodiments, antibodies specific to the enzymatic degradation, breakdown, or hydrolysis products of the modification are provided.

In certain embodiments, the present invention provides kits comprising one or more probes as described herein and instructions for detecting protein sulfenylation within cysteine residues of a protein with the provided one or more probes. In some embodiments, the probe is selected from the group consisting

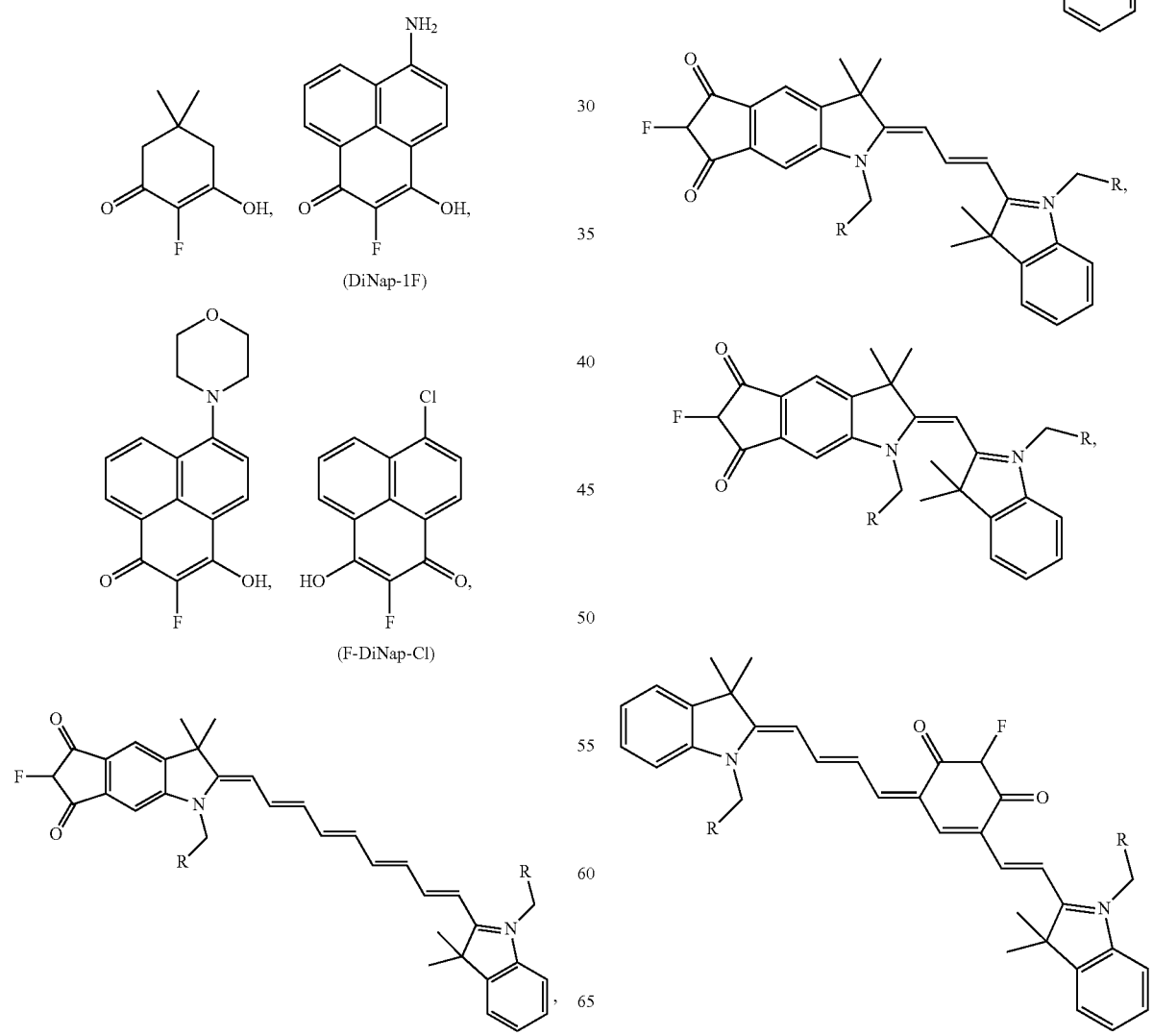

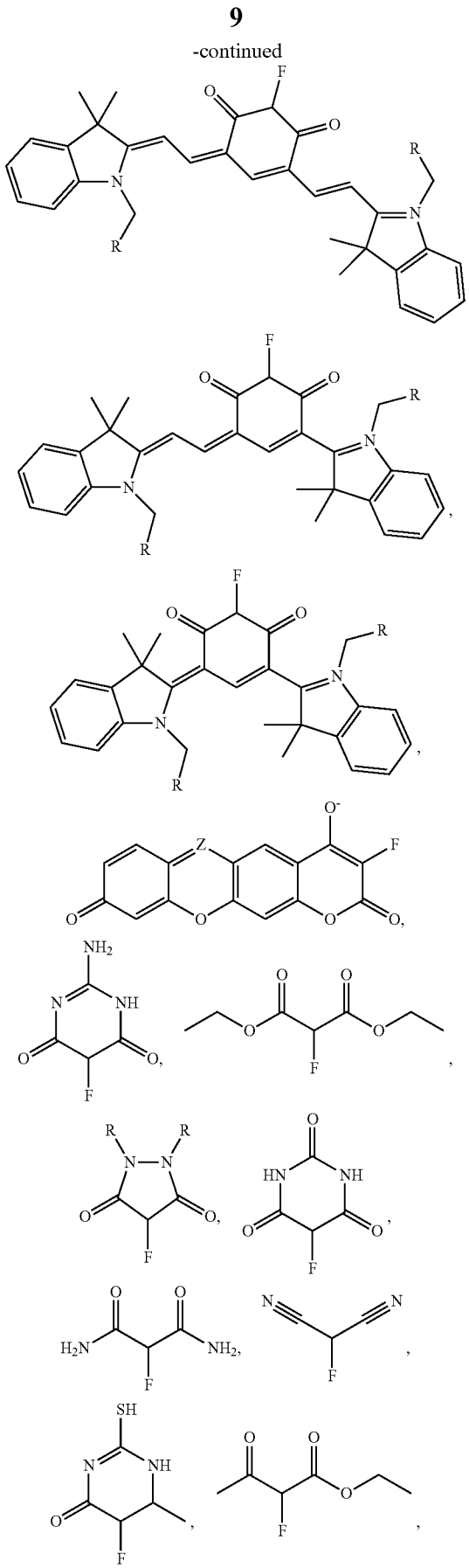

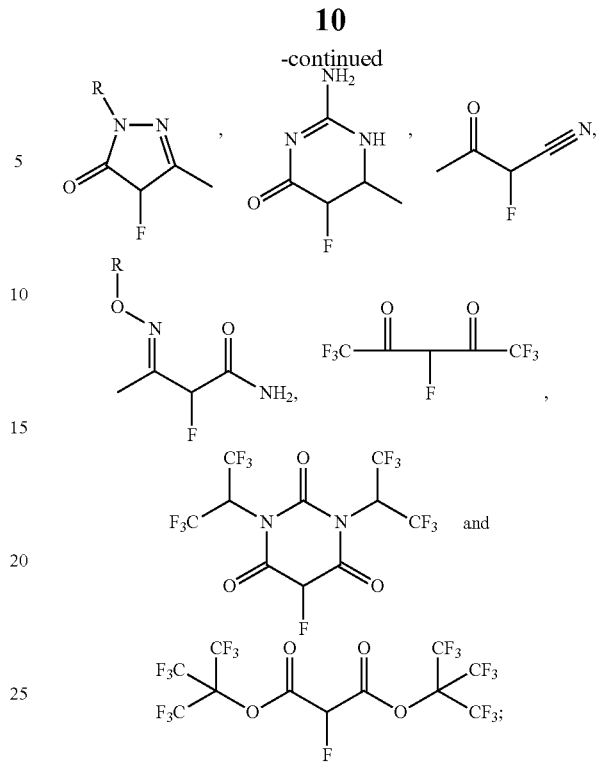

wherein Z is N or C-aryl; wherein R is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms), or a water-solubilizing group (sulfate, amine, carboxylic acid or other charged or polar functional handle).

In some embodiments, the probe is

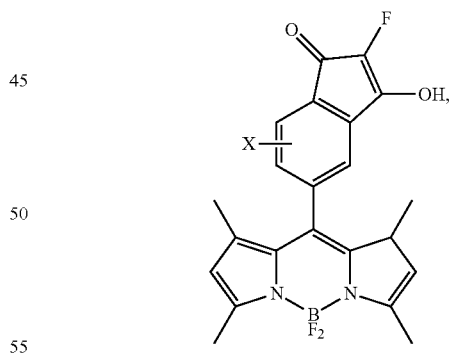

wherein X is either an electron-withdrawing chemical moiety or an electron donating chemical moiety. For example, in some embodiments wherein X is an electron-withdrawing chemical moiety, X is selected from $C(O)H$, $C(O)R_1$, $C(O)OH$, $C(O)OR_1$, $C(O)R_2$, $C(R_2)3$, $CN$, $S(O)_2OH$, $NH_3^+$, $C(O)N(R)_2$, $N(R)_3^+$, and $NO_2$; and wherein $R_1$ is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms); and wherein $R_2$ is a halogen (e.g., Cl, F, I). For example, in some embodiments wherein X is an electron-donating chemical moiety, X is selected from Oxygen, $N(R_1)_2$, $NH_2$, SH, $SR_1$, OH, $OR_1$, $NHC(O)R_1$, $R_1$, benzene, $C(H)=C(R)_2$; and wherein $R_1$ is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms).

In some embodiments, the probe is shown in FIGS. 8, 10 and/or 11.

DETAILED DESCRIPTION OF THE INVENTION

Figure 1:
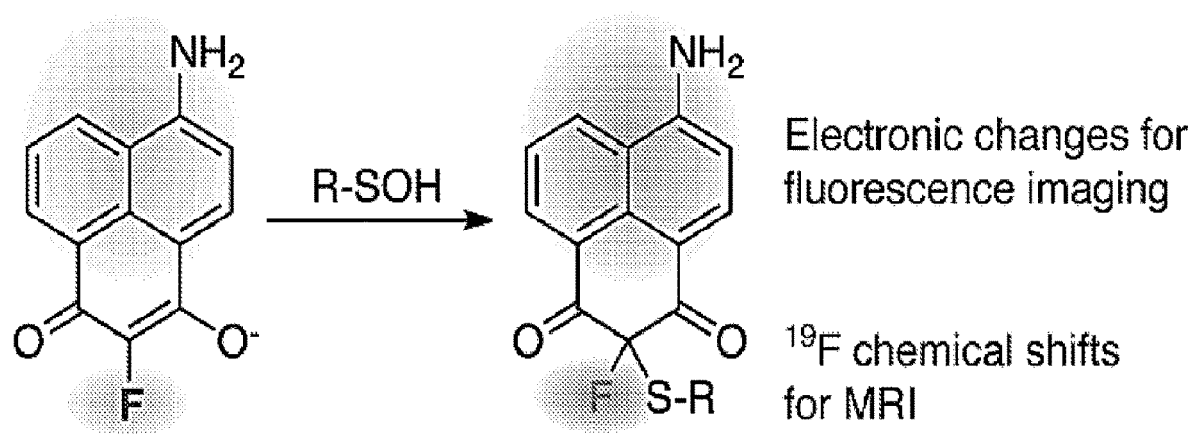
FIG. 1 shows an "enolate to di-ketone" switch for the DiNap-1F probe.

Sulfenic acids are labile, reversible post-translational modifications (PTM) formed by the oxidation of cysteine residues by hydrogen peroxide (see, e.g., Paulsen, C. E. & Carroll, K. S., 2013 Chemical Reviews 113, 4633-4679). Growth factor stimulation induces Nox activation (see, e.g., Lambeth, J. D., Nature Reviews Immunology 4, 181-189 (2004)), generating bursts of hydrogen peroxide that can react with the redox-sensitive, nucleophilic cysteines in their thiolate form (see, e.g., Klomsiri, C., et al., Antioxidants & Redox Signaling 14, 1065-1077 (2011)). One such target is the protein phosphatase PTP1B, where Nox-dependent sulfenylation inactivates catalytic residues (see, e.g., Paulsen, C. E. et al., 2012 Nature Chemical Biology 8, 57-64). This unique oxidative messaging system functions to transiently suppress phosphatase activity to amplify growth factor signals. Interestingly, the sulfenic acid formed in PTP1B is protected from overoxidation by cyclization with the amide nitrogen from the next residue forming a sulfonamide (see, e.g., Tanner, J. J., et al., 2011 Antioxidants & Redox Signaling 15, 77-97), which prevents further irreversible oxidation to sulfinic ($CysSO_2H$) and sulfonic ($CysSO_3H$) acids (see, e.g., Paulsen, C. E. & Carroll, K. S., 2013 Chemical Reviews 113, 4633-4679). Further proteomic analysis has revealed numerous other important sulfenylated proteins, including proteases, dehydrogenases, deubiquitinases and other redox-sensitive enzymes (see, e.g., Leonard, S. E., et al., 2009 Acs Chemical Biology 4, 783-799). Overall, sulfenylation is suggested to play a widespread role in immune signaling, cellular redox homeostasis, and growth factor activation. Conversely, misregulation of sulfenylation has implications on human health, including neurodegenerative and proliferative diseases (see, e.g., Paulsen, C. E. & Carroll, K. S., 2013 Chemical Reviews 113, 4633-4679).

Active methylene compounds (AMCs) such as dimedone are the primary covalent tools to study protein sulfenylation, and are limited to biochemical and proteomic analysis (see, e.g., Paulsen, C. E. & Carroll, K. S., 2013 Chemical Reviews 113, 4633-4679). Recent proteomics studies reveal a wide range of sulfenylated proteins (see, e.g., Leonard, S. E., et al., 2009 Acs Chemical Biology 4, 783-799), yet it is unclear whether sulfenylation of certain proteins is spatially or temporally regulated Immunofluorescence of dimedone-conjugated proteins suggests sulfenylation is enriched at intracellular organelles (see, e.g., Paulsen, C. E. et al., 2012 Nature Chemical Biology 8, 57-64; Seo, Y. H. & Carroll, K. S., 2009 Proceedings of the National Academy of Sciences of the United States of America 106, 16163-16168), but harsh fixation conditions and stringent washes make such analysis difficult to interpret.

Existing methods to image the levels of oxidative species (e.g., peroxide, superoxide, hypochloride) typically use non-selective 'turn-on' fluorophores. These non-ratiometric probes are difficult to quantify, and respond to an array of reactive oxygen species. Furthermore, they are not conjugated to a protein following reaction, and as such are subject to higher levels of diffusion and localization is not correlated to protein localization. The present invention provides improved methods for detecting protein oxidation/sulfenylation at both in vitro and in vivo levels. Indeed, the present invention provides a new generation of probes for live-cell ratiometric fluorescence imaging of protein oxidation/sulfenylation.

The present invention is not limited to particular types of probes for detecting cysteine oxidation and/or protein sulfenylation. In some embodiments, such probes are based on the small-molecule scaffold dimedone, an active methylene compound (AMC) derivative of 1,3-cyclohexanedione (see, e.g., Poole, L. B., et al., 2005 Bioconjugate Chemistry 16, 1624-1628). These soft nucleophiles selectively and irreversibly couple to sulfenylated cysteine residues to form stable thioethers. Current 'clickable' probes, such as DYn2 (see, e.g., Paulsen, C. E. & Carroll, K. S., 2013 Chemical Reviews 113, 4633-4679; Leonard, S. E., et al., 2009 Acs Chemical Biology 4, 783-799) and dimedone-specific antibodies (see, e.g., Seo, Y. H. & Carroll, K. S., 2009 Proceedings of the National Academy of Sciences of the United States of America 106, 16163-16168) have been used for biochemical analysis of sulfenylated proteins, as well as crude fluorescence imaging on fixed cells. However, due to the impermeability of the cell membrane towards antibodies, and since the signal from constitutively active unbound dye dominates the image, and because fixing conditions is perturbative to living cells, this approach is incompatible with live cell fluorescence microscopy.

The probes of the present invention overcome these limitations by utilizing a chemical 'switch' (FIG. 1) that alters the spectroscopic properties of the probe after sulfenic acid conjugation. Such probes leverage the reactivity of dimedone to manipulate the site of reactivity: the shared α-carbon. Such probes provide a rationally designed, mechanism-based organic dye for visualizing a post-translational modification in living cells. Furthermore, in some embodiments, $^{19}$F nuclear magnetic resonance imaging ($^{19}$F NMR/MRI) is utilized for quantifying and visualizing a post-translational modification in living cells and tissues. In some embodiments, such probes offer a multiplatform design to induce chemical and electronic changes for detection by complimentary spectroscopic imaging methods across cellular and multicellular living systems.

The probes of the present invention overcome the limitations of existing dimedone probes, depart from existing methods, and provide opportunities to visualize protein oxidation/sulfenylation in cells and tissues. Furthermore, such probes provide opportunity to quantify the sub-cellular dynamics of protein oxidation/sulfenylation, and characterize the contribution of redox chaperones in regulating in vivo sulfenylation.

Figure 9A:
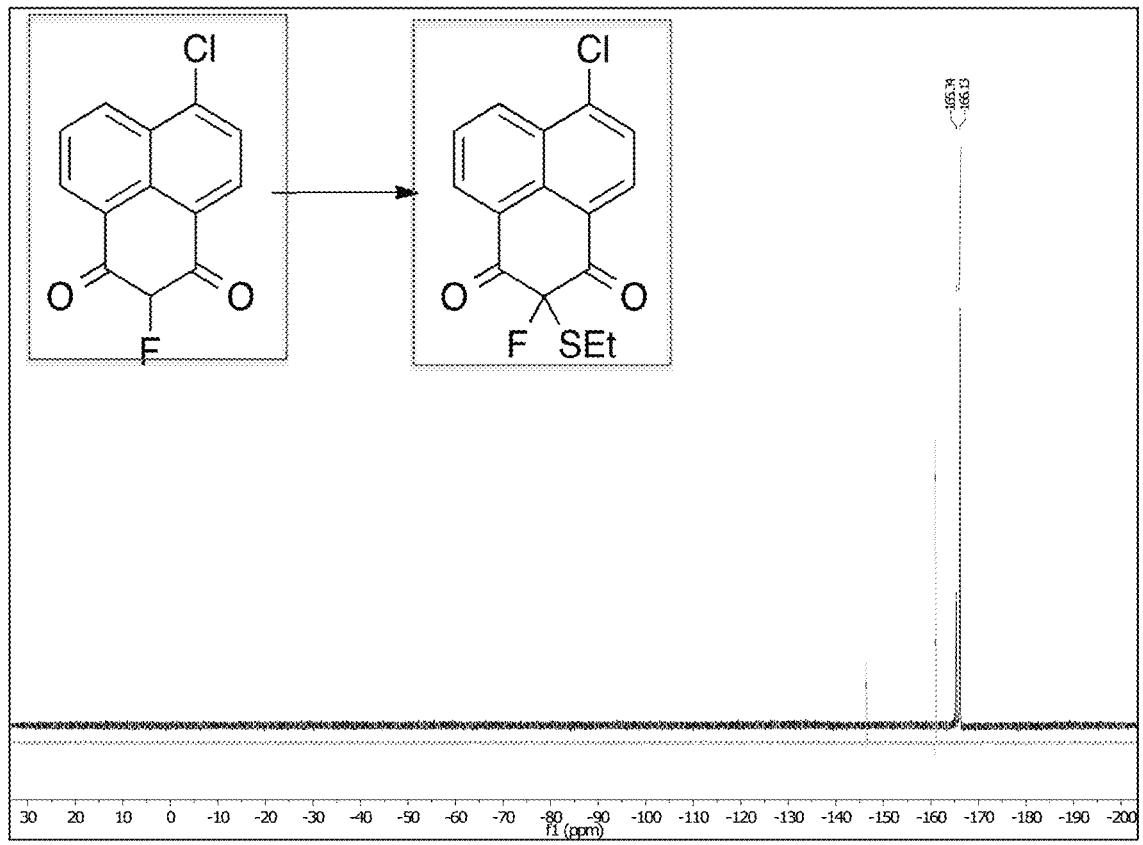
FIG. 9A-C shows experimentally determined shifts in 19F NMR signals between A) F-DiNaps bearing a morpholino pendant substituent and EtSF DiNap bearing a morpholino pendant substituent, B) F-DiNaps bearing a chloro substituent and EtSF DiNap bearing a chloro substituent, and C) F-DiNaps bearing an amino substituent and MeSF DiNap bearing an amino substituent on the rings.
Figure 9B:
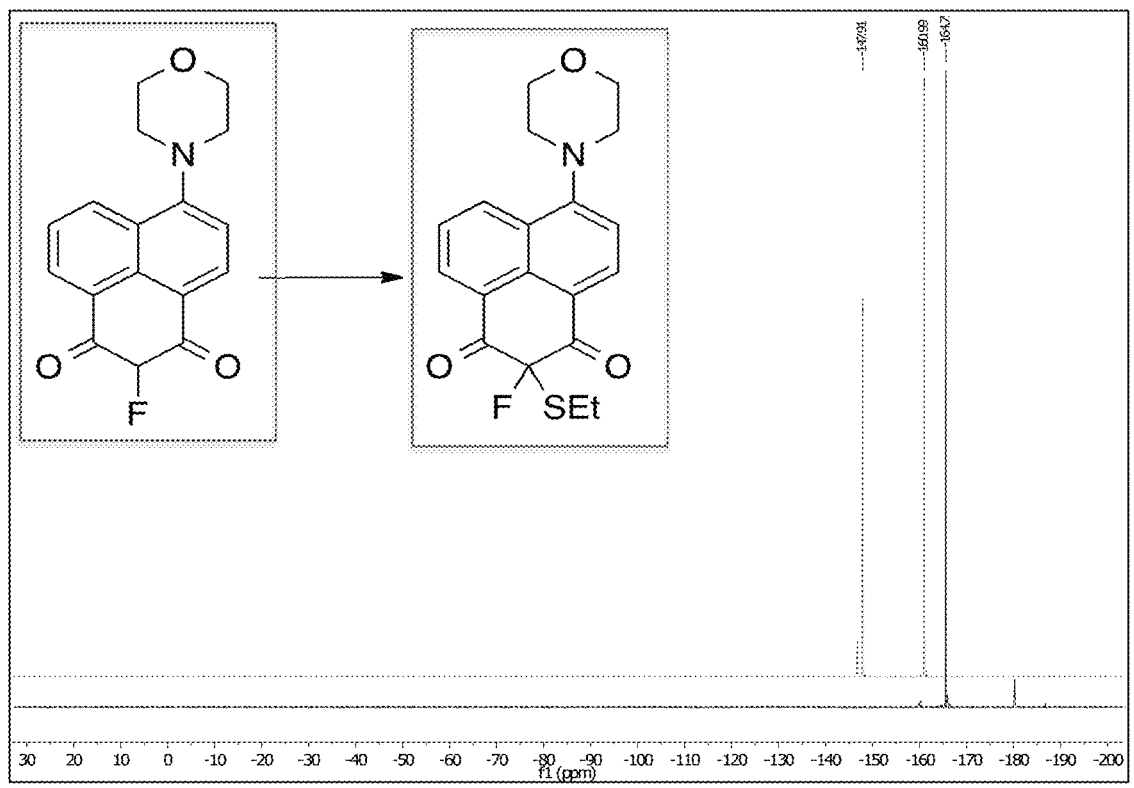
Figure 9C:
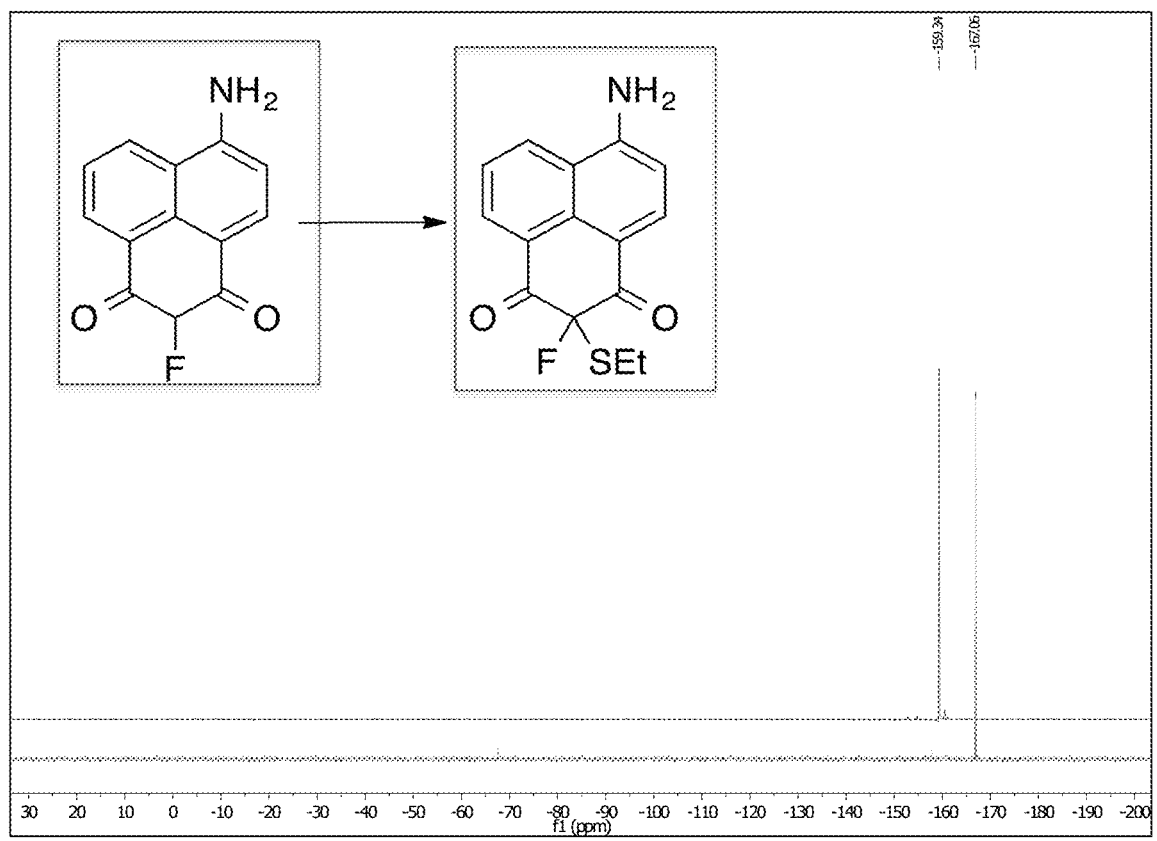
Figure 13:
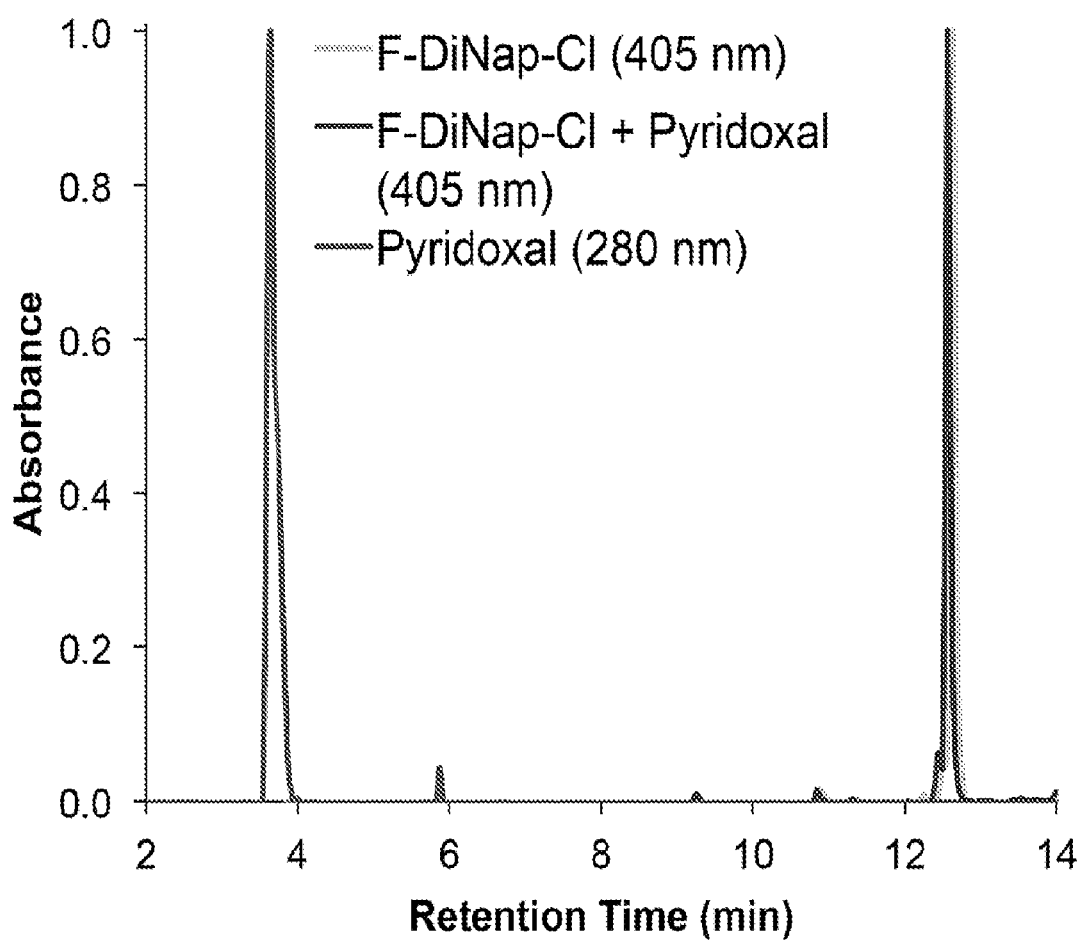
FIG. 13 shows gray-scaled high-performance liquid chromatography traces of solutions of F-DiNap-Cl before and following exposure with pyridoxal.
Figure 14:
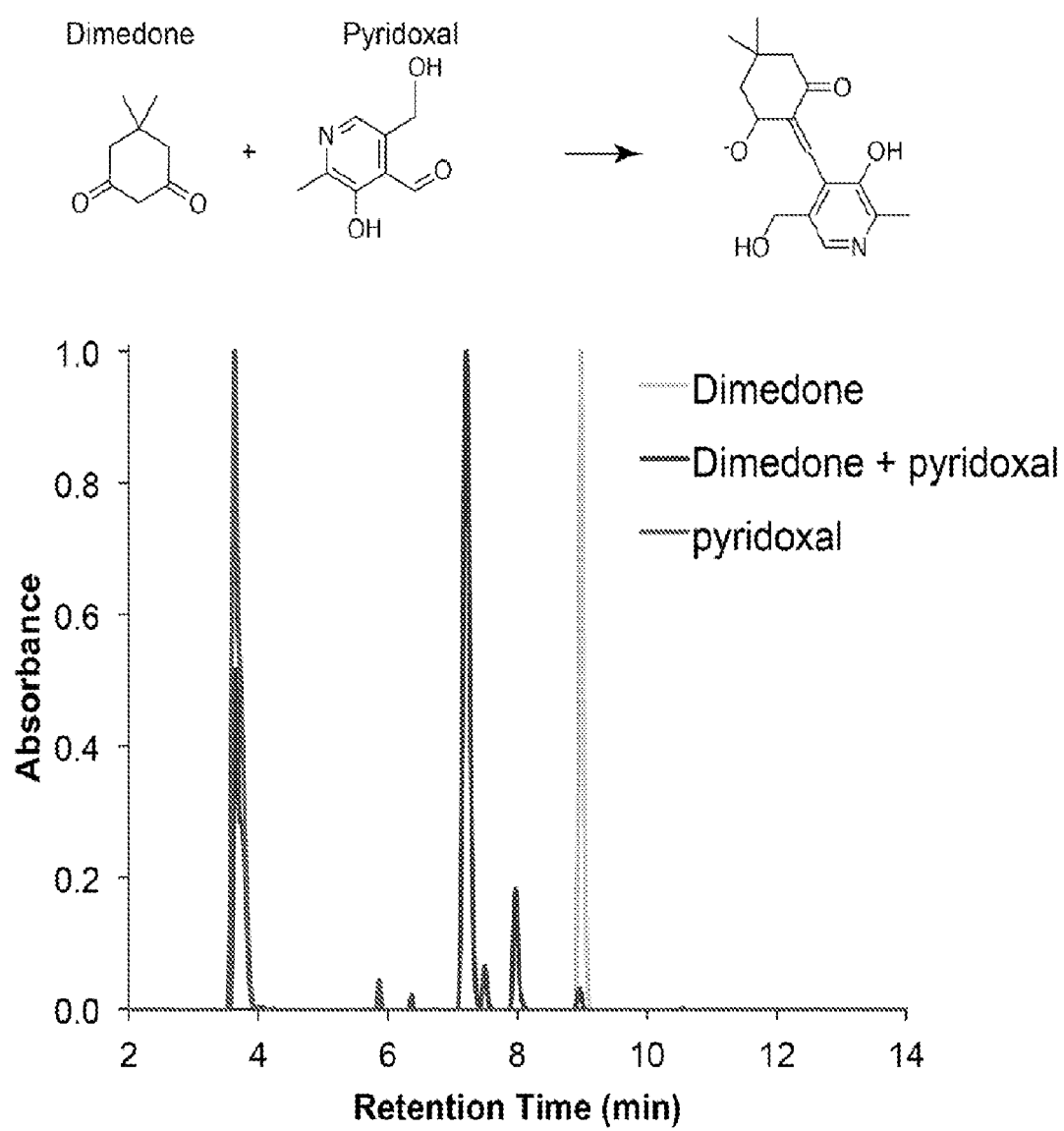
FIG. 14 shows gray-scaled high-performance liquid chromatography traces of solutions of dimedone before and following exposure with pyridoxal.

In certain embodiments, the present invention provides the following probes for detecting protein sulfenylation/cysteine oxidation having a dimedone based structure:

Experiments conducted during the course of developing embodiments for the present invention demonstrated that upon conjugation to sulfenic acid, the DiNap-1F probe switched to an altered electronic state, inducing a >2-fold excitation ratiometric fluorescence change after only a few minutes. FIG. 9 shows spectroscopic properties of different probes prior to and following exposure to R—SOH. FIG. 13 shows spectroscopic properties of F-DiNap-Cl before and following exposure with pyridoxal. FIG. 14 shows spectroscopic properties of dimedone before and following exposure with pyridoxal. In these experiments, the incorporation of a blocking group inhibits other two-proton processes, such as the Knoevenagel condensation of AMCs with aldehydes. F-AMC analogues display a higher degree of selectivity.

In certain embodiments, the present invention provides the following probes for detecting protein sulfenylation/cysteine oxidation having a cyanine based structure:

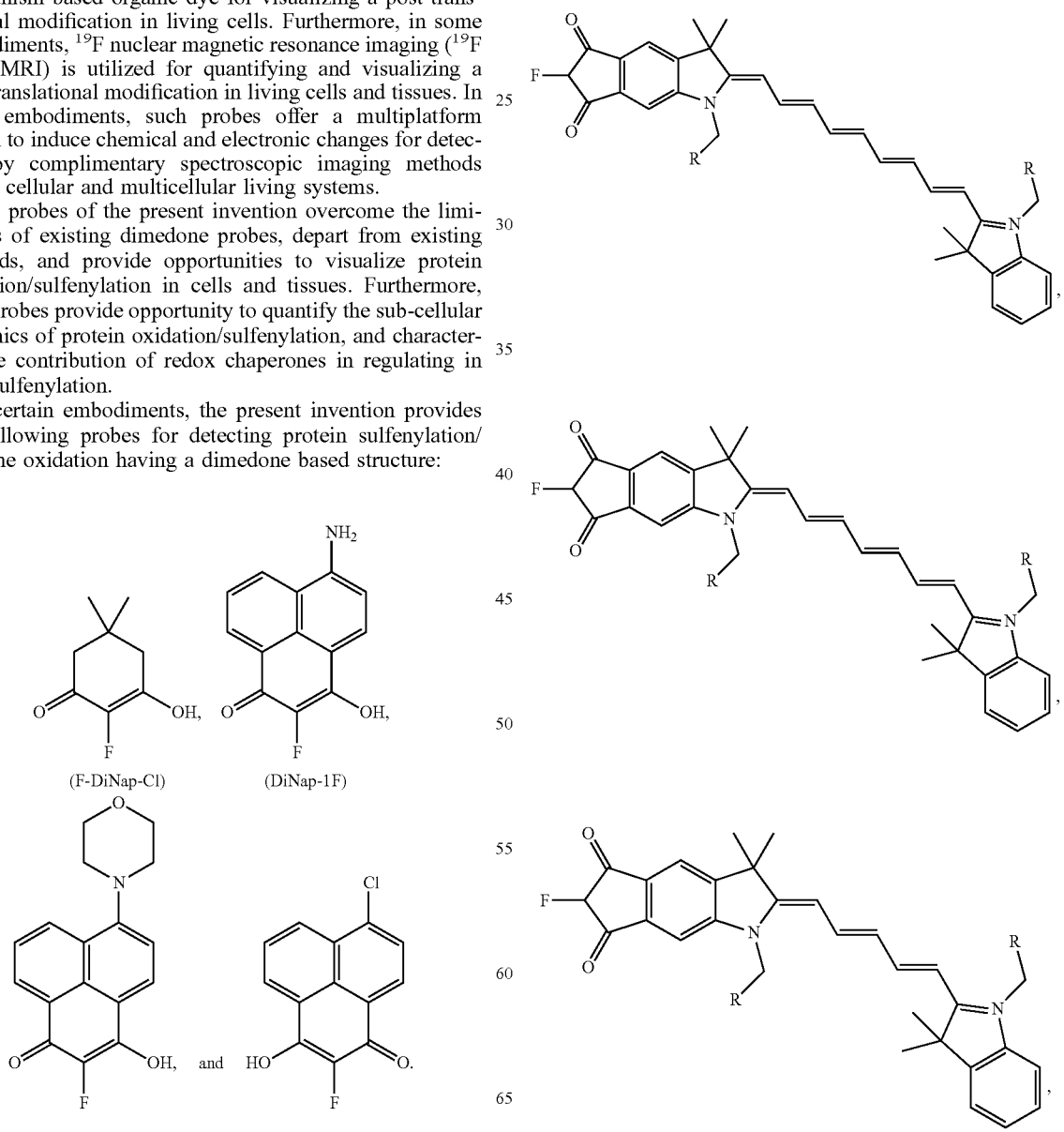

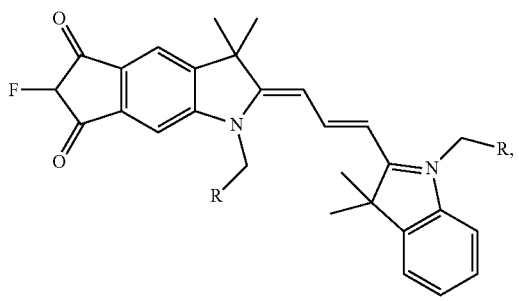

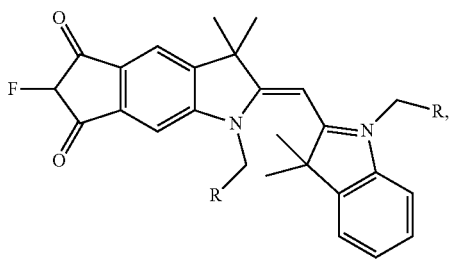

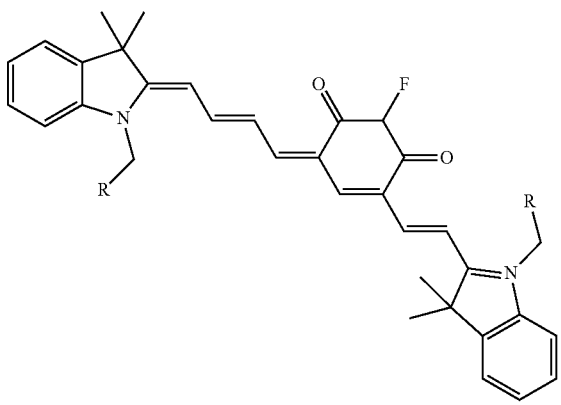

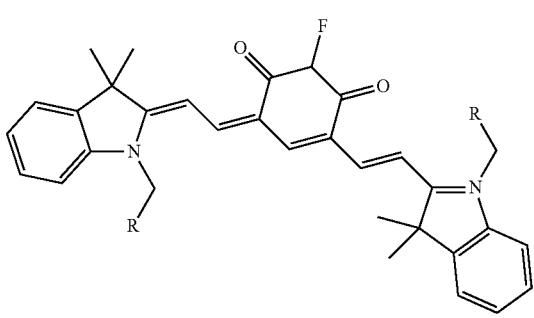

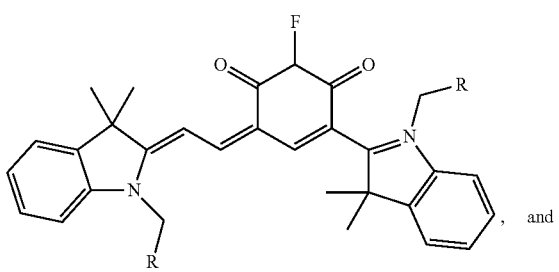

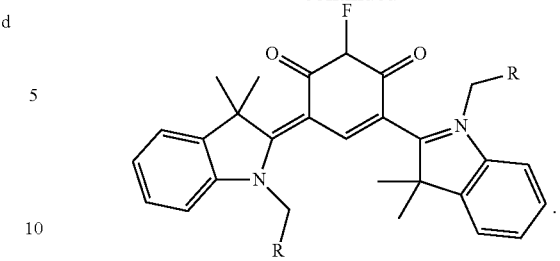

The cyanine based probes are designed to modulate the fluorophore properties due to electronic changes after sulfenic acid conjugation, with by direct insertion of the dimedone scaffold within the conjugated methine, or by terminal coupling to the end of the fluorophore. Such "photoswitchable" probes enable super-resolution stochastic imaging of cellular protein sulfenylation.

In certain embodiments, the present invention provides the following probes for detecting protein sulfenylation/cysteine oxidation having a BODIPY based structure:

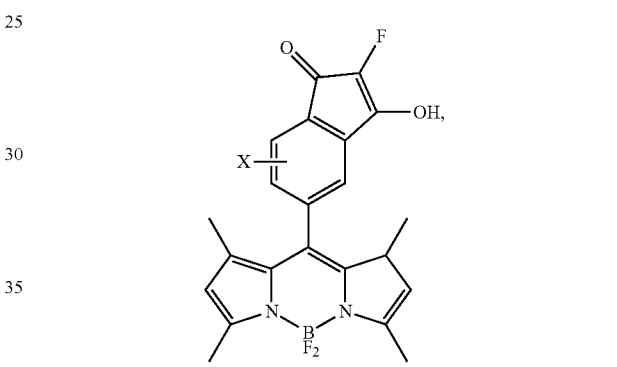

wherein X is either an electron-withdrawing chemical moiety or an electron donating chemical moiety. For example, in some embodiments wherein X is an electron-withdrawing chemical moiety, X is selected from C(O)H, C(O)R$_1$, C(O)OH, C(O)OR$_1$, C(O)R$_2$, C(R$_2$)3, CN, S(O)$_2$OH, NH$_3^+$, C(O)N(R)$_2$, N(R)$_3^+$, and NO$_2$; and wherein R$_1$ is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms); and wherein R$_2$ is a halogen (e.g., Cl, F, I). For example, in some embodiments wherein X is an electron-donating chemical moiety, X is selected from Oxygen, N(R$_1$)$_2$, NH$_2$, SH, SR$_1$, OH, OR$_1$, NHC(O)R$_1$, R$_1$, benzene, C(H)=C(R)$_2$; and wherein R$_1$ is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms).

The BODIPY based probes exhibit large shifts in quantum yield depending on the reduction potential of the group at the meso position by photoelectron transfer (PET). By installing the 2-fluoro-1,3-dicarbonyl on an electron-rich aromatic ring, the unbound enolate form suppresses fluorescence by PET. By switching from an electron-rich enolate to an electron-poor diketone, this eliminates PET and restores fluorescence. In some embodiments, such probes are coupled to a second FRET donor or acceptor for use as a ratiometric probe.

In certain embodiments, the present invention provides the following probes for detecting protein sulfenylation/cysteine oxidation having a xanthene based structure:

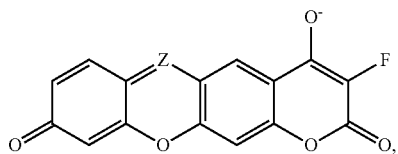

wherein Z is N or C-aryl. In some embodiments, upon conjugation, the stable, negatively charged aromatic ester of a xanthene based probe converts to a dicarbonyl, which is also an active ester, resulting in rapid hydrolysis of the ester bond and formation of the fluorescent dye. The rate of hydrolysis is not rate-limiting.

In certain embodiments, the present invention provides $^{19}$F-AMC probes for detecting protein sulfenylation/cysteine oxidation. Examples of such $^{19}$F-AMC probes include, but are not limited to,

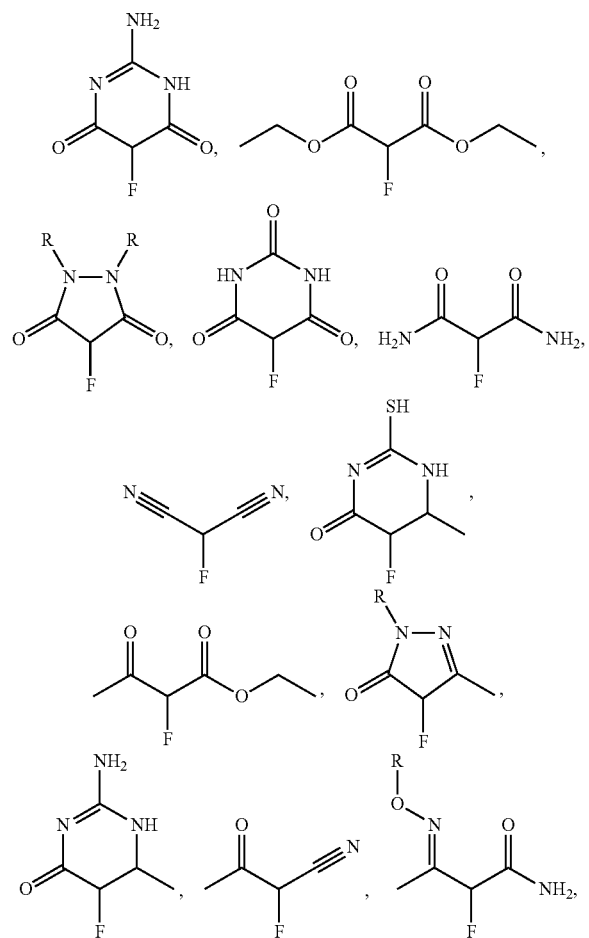

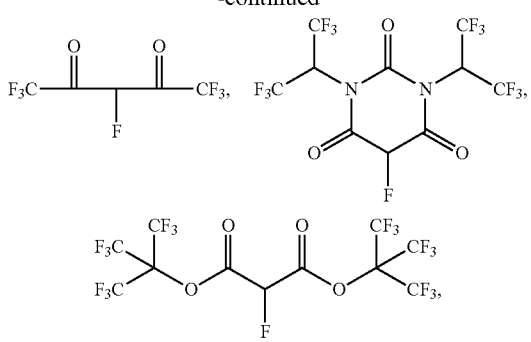

(see, also, FIGS. 8, 9, and 10), wherein R is independently selected from hydrogen, an alkyl, vinyl, allyl, alkynyl, or aryl group having between 1-10 carbons (saturated or unsaturated) (substituted or non substituted) (having or not having one or more heteroatoms), or an aromatic or non aromatic ring structure (substituted or non substituted) (substituted or non substituted) (having or not having one or more heteroatoms).

Figure 11:
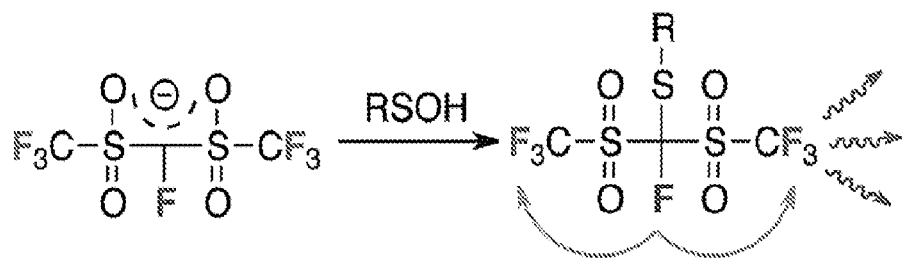
FIG. 11A-C shows examples of ways the 19F NMR signal can be amplified.
FIG. 11D shows expected small animal MRI visualization of in vivo sulfenylation.
Figure 11:
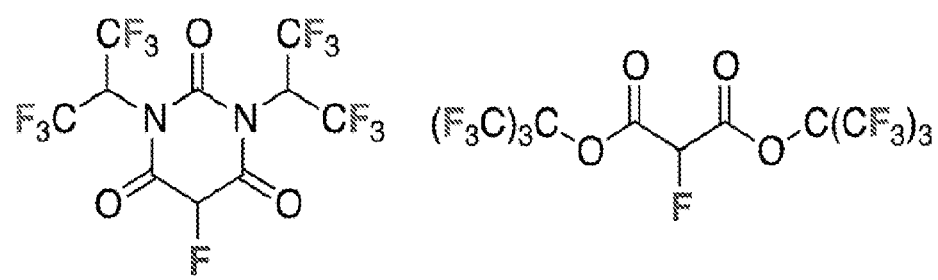
Figure 11:
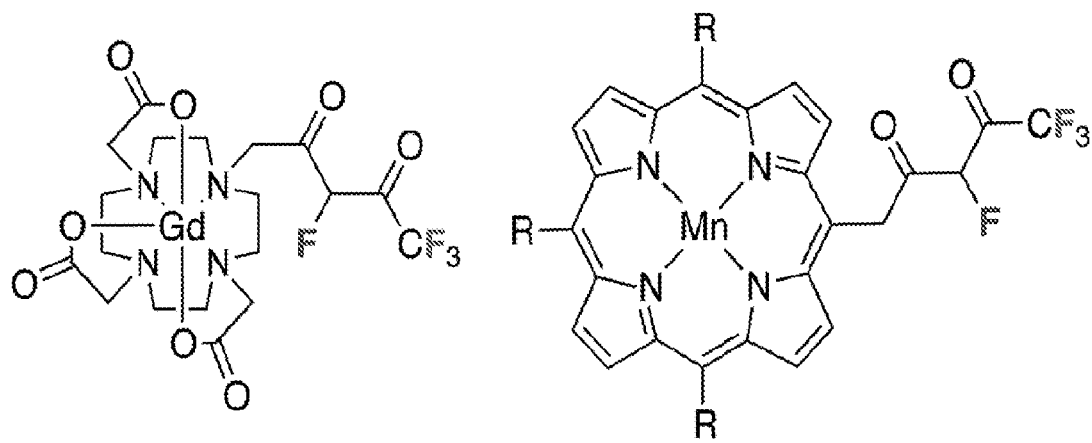
Figure 11:
Figure 11:
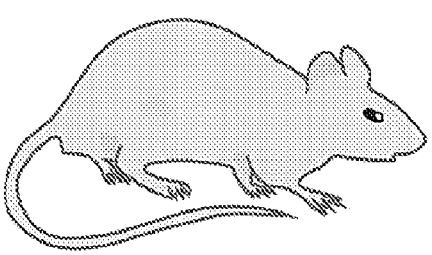
Figure 11:

In some embodiments, the present invention provides methods utilizing such $^{19}$F-AMC probes for imaging protein sulfenylation in vivo using animal models of protein oxidation and disease (FIG. 11D). In some embodiments, such methods will utilize mammalian subjects as in vivo models (e.g., mouse subjects, human subjects, etc.). In some embodiments, simple genetic systems in bacteria and yeast will be analyzed in NMR sample tubes using a traditional $^{19}$F-NMR instrument. For example, the conserved cytosolic protein DJ-1 (PARK7) will be analyzed with such methods. DJ-1 (PARK7) is mutated in early-onset Parkinson's disease, and protects cells from oxidative stress (see, e.g., Bonifati, V. et al., 2003 Science 299, 256-259). For example, the bacterial homologue, YajL will be analyzed with such methods. YajL has been shown to form mixed disulfides with a number of cytosolic proteins. Formation of these conjugates is blocked by dimedone, suggesting YajL preferentially reacts with sulfenic acids, perhaps as part of a catalytic cycle to speed the reduction of oxidized species (see, e.g., Gautier, V. et al., 2012 Journal of Molecular Biology 421, 662-670). Such methods will investigate the enigmatic function of mammalian DJ-1 in preventing oxidative stress and neurodegeneration.

Table 1 shows probes of the present invention in unreacted form and following interaction with a sulfenylated protein (wherein R represents a cysteine amino acid).

TABLE 1

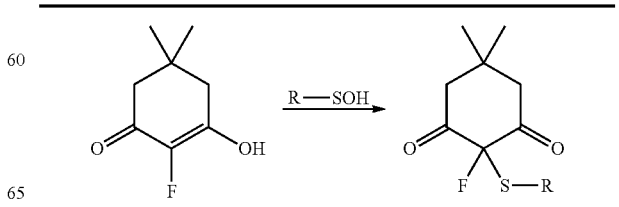

TABLE 1-continued

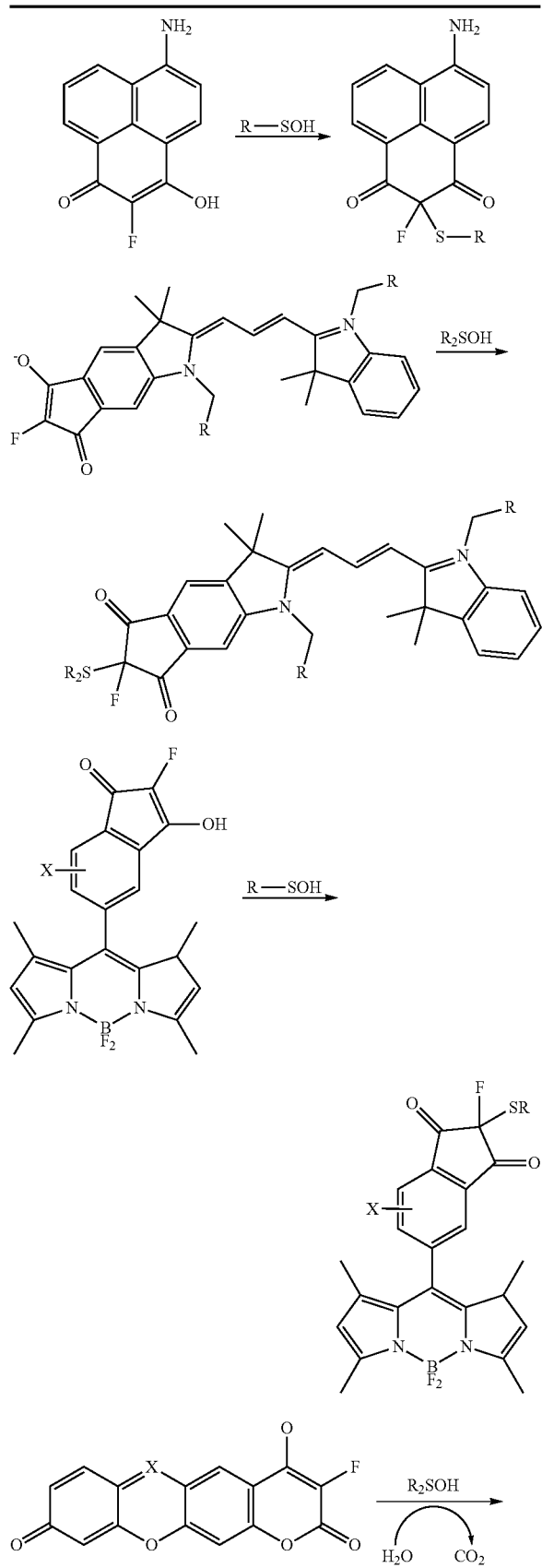

TABLE 1-continued

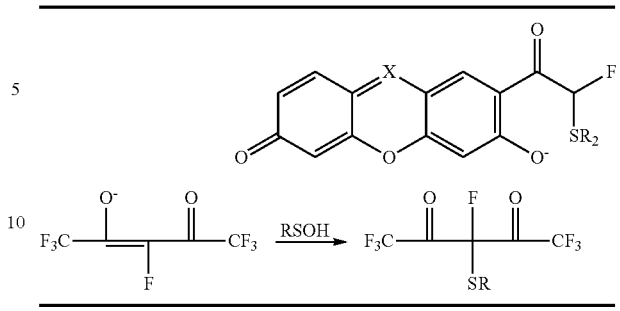

In certain embodiments, the present invention provides compositions comprising one or more of the probes of the present invention for detecting protein sulfenylation.

In certain embodiments, the "enolate-to-diketone" switch is replaced with an "enolate-to-dicarbonyl" switch. In some embodiments, another analogous, relevant functional group changes will occur (e.g., through loss of aromaticity (e.g., resulting in "caged" reactive groups to become labile)).

In certain embodiments, the present invention provides methods for detecting protein sulfenylation at sulfenylated cysteine residues of a protein, comprising providing a biological sample comprising one or more proteins having cysteine residues and a composition comprising a probe having a chemical moiety configured to switch from an enolate form to a di-ketone form upon conjugation with a sulfenic acid side chain of a cysteine residue, exposing the composition to the biological sample such that an interaction between the probe and a sulfenic acid side chain of a cysteine residue results in conjugation of the probe with the sulfenic acid side chain, measuring the spectroscopic properties of the probe following exposure of the composition to the biological sample, wherein and characterizing the cysteine residues of the protein as having undegone sulfenylation if the measuring indicates the presence of the probe in a di-ketone form. In some embodiments, the methods further comprise quantifying the amount of protein sulfenylation.

In some embodiments, the protein can subsequently be separated from the sample and identified. In some embodiments, the methods further comprise identifying the protein having been characterized as having undergone sulfenylation and/or identifying the exact amino acid sites on the protein having been characterized as having undergone sulfenylation.

Such methods are not limited a particular manner of measuring the spectroscopic properties of the exposed probe. In some embodiments, ratiometric fluorescence imaging is used to measure the spectroscopic properties of the exposed probe. In some embodiments, $^{19}$F-NMR imaging is used to measure the spectroscopic properties of the exposed probe. In some embodiments, $^{1}$H-NMR imaging is used to measure the spectroscopic properties of the exposed probe.

As used herein, the term "nuclear magnetic resonance (NMR) signal" is intended to mean an output representing the frequency of energy absorbed by a population of magnetically equivalent atoms in a magnetic field, the magnitude of energy absorbed at the frequency by the population and distribution of frequencies around a central frequency. The frequency of energy absorbed by with an atom in a magnetic field can be determined from the location of a peak in an NMR spectrum. The magnitude of energy absorbed at a frequency by a population of atoms can be determined from relative peak intensity. The distribution of frequencies around a central frequency can be determined from the shape of a peak in an NMR spectrum. Accordingly, a collection of nuclear magnetic resonance signals for a molecule or sample containing multiple atoms can be represented in an NMR spectrum, as an atom having a signal of characteristic frequency, intensity and line-shape. Furthermore, additional parameters that may be measured are the T1 relaxation rate (spin-lattice relaxation time) and the T2 (spin-spin relaxation time).

Such methods are not limited to a particular type of biological sample comprising proteins having cysteine residues. In some embodiments, the sample comprises proteins, metabolites, and/or materials having thiol groups. In some embodiments, the sample is an in vitro sample. In some embodiments, the sample is an in vitro sample having proteins having cysteine residues. In some embodiments, the sample is an ex vivo sample. In some embodiments, the sample is an ex vivo sample obtained from a subject. In some embodiments, the sample is an ex vivo sample obtained from a subject suspected of experiencing aberrant protein sulfenylation. In some embodiments, the sample is an in vivo sample. In some embodiments, the in vivo sample is a living subject (e.g., a human subject, a mouse subject). In some embodiments, the living subject is suspected of experiencing aberrant protein sulfenylation. In some embodiments, the sample is a clinical biopsy from a subject (e.g., a human subject).

Such methods can be used for any number of purposes.

In some embodiments, the methods are used to determine if a subject (e.g., a human subject) is experiencing protein sulfenylation.

In some embodiments, such methods can be used to evaluate the efficacy of a particular type of treatment for inhibiting or facilitating protein sulfenylation.

In certain embodiments, the present invention provides methods for detecting protein sulfenylation within cysteine residues of a protein.

In certain embodiments, the present invention provides methods for identifying proteins having undergone sulfenylation and/or to annotate/profile particular localization of such sulfenylation.

In certain embodiments, the present invention provides methods to determine the spatiotemporal cellular localization of normal or aberrant sulfenylation used in the technique of fluorescence microscopy.

In certain embodiments, the present invention provides methods for screening biological samples for the presence of sulfenylated proteins.

In certain embodiments, the present invention provides methods for identifying proteins having undergone sulfenylation and/or to annotate/profile particular locations of such sulfenylation. Indeed, in some embodiments, the methods further comprise identifying the protein having been characterized as having undergone sulfenylation and/or identifying the exact amino acid sites on the protein having been characterized as having undergone sulfenylation. For example, in some embodiments, biological samples (e.g., complex cell lysates or tissue samples) are treated with a probe of the present invention, prepared for mass spectrometric analysis, and peptidic fragments separated by liquid chromatography (LC) followed by mass spectrometry. In some embodiments, the methods further involve proteomic analysis using bioinformatics and the raw data is searched against, for example, a defined database to identify particular proteins and to detect peptides bearing the conjugated probe to annotate and profile sites of labeling.

"Mass spectrometry," as used herein, refers to a method comprising employing an ionization source to generate gas phase ions from a biological entity of a sample presented on a biologically active surface, and detecting the gas phase ions with an ion detector. Comparison of the time the gas phase ions take to reach the ion detector from the moment of ionization with a calibration equation derived from at least one molecule of known mass allows the calculation of the estimated mass to charge ratio of the ion being detected. The term "mass spectrometer" refers to a gas phase ion spectrometer that includes an inlet system, an ionization source, an ion optic assembly, a mass analyzer, and a detector.

In certain embodiments, the probes will contain elements with stable and well-defined isotopic distribution patterns (e.g. Cl, Br). In other embodiments, the probes will contain groups that will have known fragmentation patterns. In other embodiments, it will contain both isotopic distribution and fragmentation patterns for unenriched identification of sulfenylated proteins.

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

In certain embodiments, the methods of the present invention are used to assist in characterizing disorders involving protein sulfenylation (e.g., strokes, chronic degenerative diseases, including Parkinson's and Alzheimer's disease; Amyotrophic Lateral Sclerosis (ALS); cancer).

In some embodiments, such methods for sulfenylation detection are used to identify pharmaceutical agents (e.g., compounds, medicaments) capable of preventing or facilitating protein sulfenylation. The present invention is not limited to particular methods for identifying pharmaceutical agents capable of preventing or facilitating protein sulfenylation. In some embodiments, identification of pharmaceutical agents capable of preventing or facilitating protein sulfenylation involves, for example, exposing a sample having proteins having cysteine residues known to undergo sulfenylation to a pharmaceutical agent, detecting the presence or absence of sulfenylation with the methods of the present invention, and identifying such pharmaceutical agent as being capable of preventing or inducing protein sulfenylation if such methods are able or unable to detect sulfenylation.

In some embodiments, pharmaceutical agents identified as sulfenylation inhibitors are further characterized with regard to its inhibitory effect on specific proteins. In some embodiments, such pharmaceutical agents identified as sulfenylation inhibitors are used in methods for treating subjects (e.g., human patients) suffering from disorders involving the aberrant occurrence of protein sulfenylation.

In some embodiments, pharmaceutical agents identified as sulfenylation facilitators are further characterized with regard to its facilitating effect on specific proteins. In some embodiments, such pharmaceutical agents identified as sulfenylation facilitators are used in methods for treating subjects (e.g., human patients) suffering from disorders involving the aberrant occurrence of protein sulfenylation.

In certain embodiments, the present invention provides kits for detecting protein sulfenylation. In some embodiments, the kits include, for example, one or more of the described probes. In some embodiments, such probes are provided within a composition. In some embodiments, the kits further comprise instructions for utilizing the described probes for detecting the presence or absence of protein sulfenylation.

EXPERIMENTAL

Example I

Dimedone was first shown to react with sulfenic acids in the 1960s (see, e.g., Allison, W. S., 1976 Accounts of Chemical Research 9, 293-299), yet until recently there were no significant advancements. In the last few years several groups have reported alkynyl probes such as DYn (FIG. 2a) for click chemistry conjugation, or other reporter substitutions at the distal end of the ring, like biotin or fluorescein (see, e.g., Leonard, S. E., et al., 2009 Acs Chemical Biology 4, 783-799; Poole, L. B., et al., 2005 Bioconjugate Chemistry 16, 1624-1628). In parallel, monoclonal dimedone-reactive antibodies have been developed that allow direct detection of covalent dimedone adducts by western blot and immunofluorescence (see, e.g., Seo, Y. H. & Carroll, K. S., 2009 PNAS 106, 16163-16168). These probes have also been used for enrichment and analysis by mass spectrometry, providing the first in vivo profile of sulfenylated proteins (see, e.g., Leonard, S. E., et al., 2009 Acs Chemical Biology 4, 783-799), While dimedone has been well studied, the closely related 1,3-cyclopentanediones were also shown to be chemoselective sulfenylation probes (see, e.g., Qian, J. et al., 2011 Chemical Communications 47, 9203-9205). It was shown that acyclic AMCs, like alkyl acetoacetate, also conjugate to sulfenic acids (sec, e.g., Qian, J. et al., 2012 Chemical Communications 48, 4091-4093). Accordingly, experiments conducted during the course of developing embodiments for the present invention developed other AMCs that enhance reactivity by modulating the α-carbon $pK_a$. Despite the emerging importance of sulfenic acids in biological systems, there has been no comprehensive survey of other AMC scaffolds.

Figure 2:
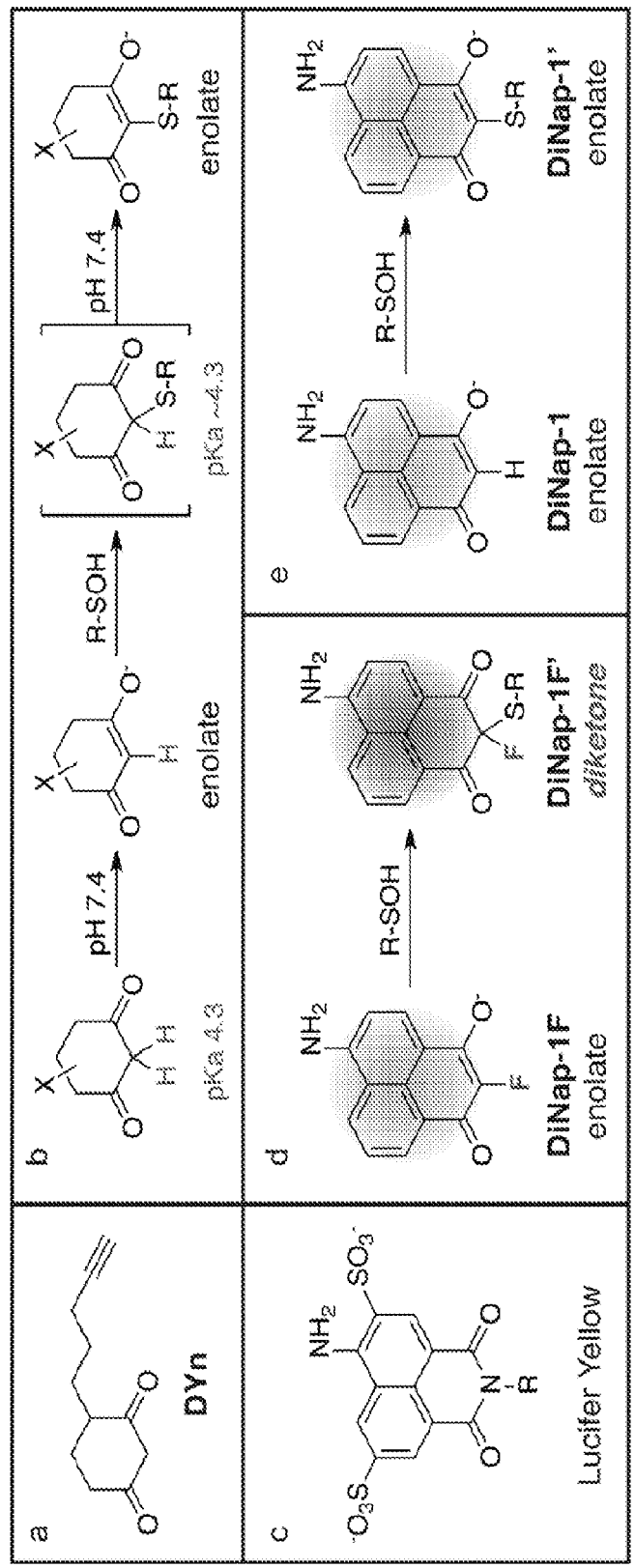
FIG. 2A-E shows the mechanistic rationale for the DiNap-1F probe.

An AMC was designed that induces a chemical switch after conjugation to a sulfenic acid, resulting in a large chemical and electronic perturbation. Dimedone has an extremely low $pK_a$ for a carbon acid (4.3) (see, e.g., Qian, J. et al., 2011 Chemical Communications 47, 9203-9205), rendering it completely deprotonated at physiological pH. As shown in FIG. 2b, dimedone reacts in its enolate form with sulfenic acids to form a stable thioether linkage, and passes through a transient diketone intermediate before it undergoes a second deprotonation to return to the enolate form. It was hypothesized that if this second deprotonation could be blocked, the probe could be trapped in its intermediate state as the diketone, and new chemical and electronic properties would be imparted.

Next, structures of common fluorophores were surveyed, and Lucifer Yellow (FIG. 2c) was selected for an initial trial due to its structural similarity to dimedone (see, e.g., Lavis, L. D. & Raines, R. T., 2008 Acs Chemical Biology 3, 142-155). Replacing the imide portion with the AMC of dimedone was envisioned, bridging the conjugated fluorophore with the reactive α-carbon. Next, the chemical switch was installed by replacing of one of the two α-protons of dimedone with a small blocking group (either a methyl group or a fluorine). Upon conjugation, the blocking group rendered the dicarbonyl unable to deprotonate a second time, trapping it in the diketone form (FIG. 2d), while the unblocked compound would return to the enolate (FIG. 2e). This enolate-to-diketone conversion resulted in an increased dipole and reduced conjugation, potentially inducing a distinct spectroscopic change.

Figure 3:
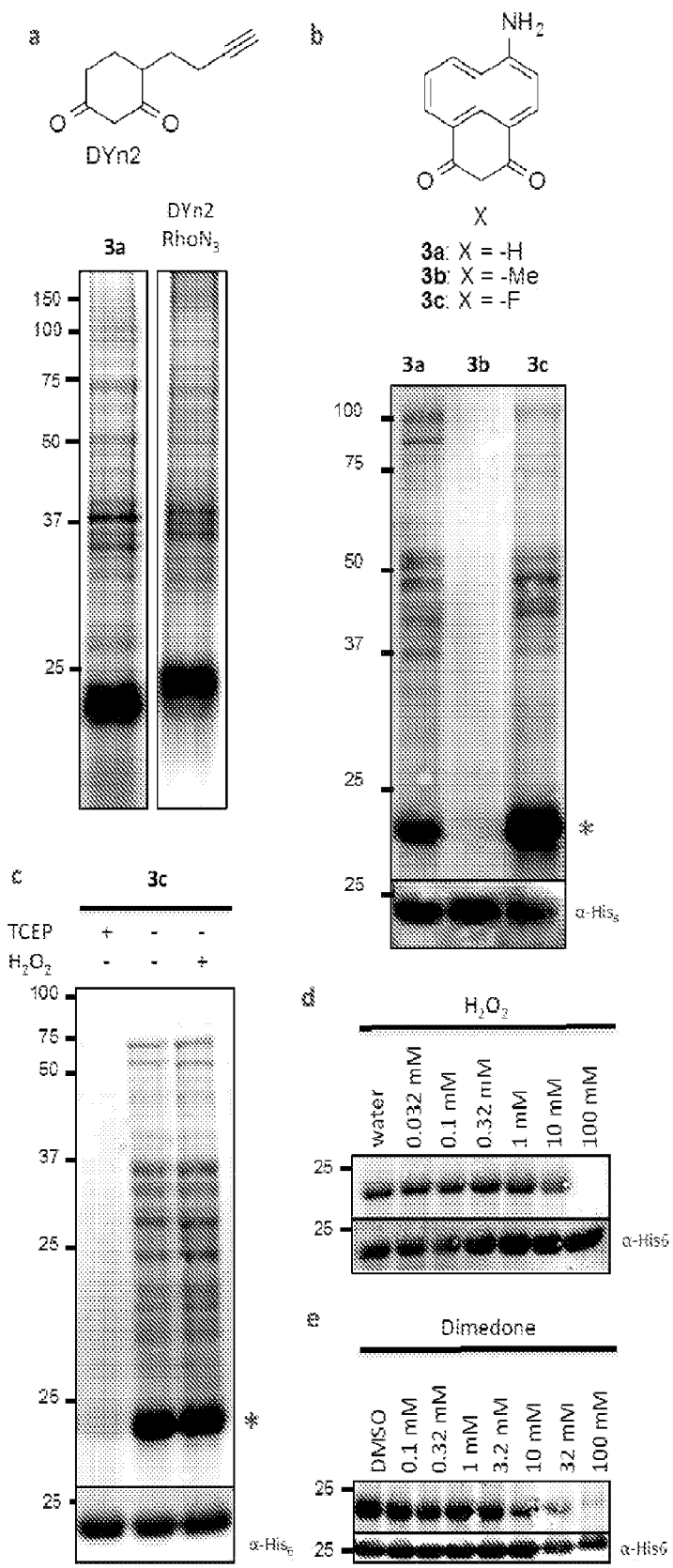
FIG. 3A-E shows labeling of BL21 cell lysates overexpressing AhpC C166S asterisk).
Figure 4:
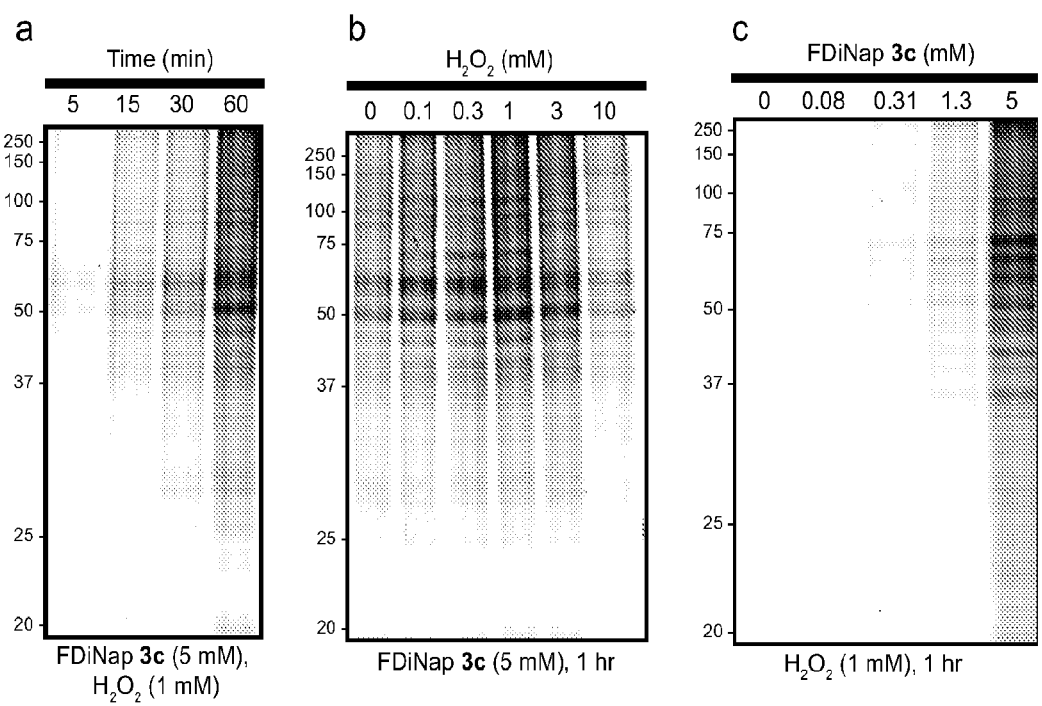
FIG. 4A-C shows labeling of live HEK293T cells with DiNap1F as a function of time and H2O2.

A small series of derivatives was next synthesized, including DiNap-1F (FIG. 2d) and control compound DiNap-1 (FIG. 2e) in a simple two-step procedure from the commercially available bromonaphthalic anhydride. FIG. 3A-E shows labeling of BL21 cell lysates overexpressing AhpC C166S (asterisk). As seen in FIGS. 3A and B, DiNap-1, DiNap-1F, DiNap-1methyl, and Dyn2 $RhoN_3$ were shown to efficiently label many endogenous sulfenylated proteins in bacterial cell lysates, including AhpC C166S, a model sulfenylated peroxiredoxin (see, e.g., Qian, J. et al., Chemical Communications 48, 4091-4093). DiNap-1F displayed the nearly identical labeling profile to the alkynyl dimedone DYn visualized after rhodamine-azide click conjugation (FIGS. 3A and 3B). A slight mass shift is observed that corresponds to the ~1 kD the additional size of the click-conjugated probe. Furthermore, labeling was eliminated by pre-treatment with TCEP, and moderately increased with low concentrations of peroxide (FIG. 3C). Conversely, higher concentrations of peroxide decreased labeling, potentially as sulfenic acids get irreversibly oxidized to sulfinic ($CysSO_2H$) and sulfonic ($CysSO_3H$) acids (FIG. 3D). Additionally, dimedone effectively competed with DiNap-1F labeling, demonstrating a similar profile of cellular proteins (FIG. 3E). Finally, live mammalian cells were similarly labeled efficiently with DiNap-1F, validating cell permeability and demonstrating time and concentration dependence (FIG. 3e). FIG. 4A-C shows labeling of live HEK293T cells with DiNap1F as a function of time and H2O2. Taken together, these results indicate that DiNap-1F labels a similar profile of sulfenic acids, and α-fluorine substitution does not hinder reactivity.

Figure 5:
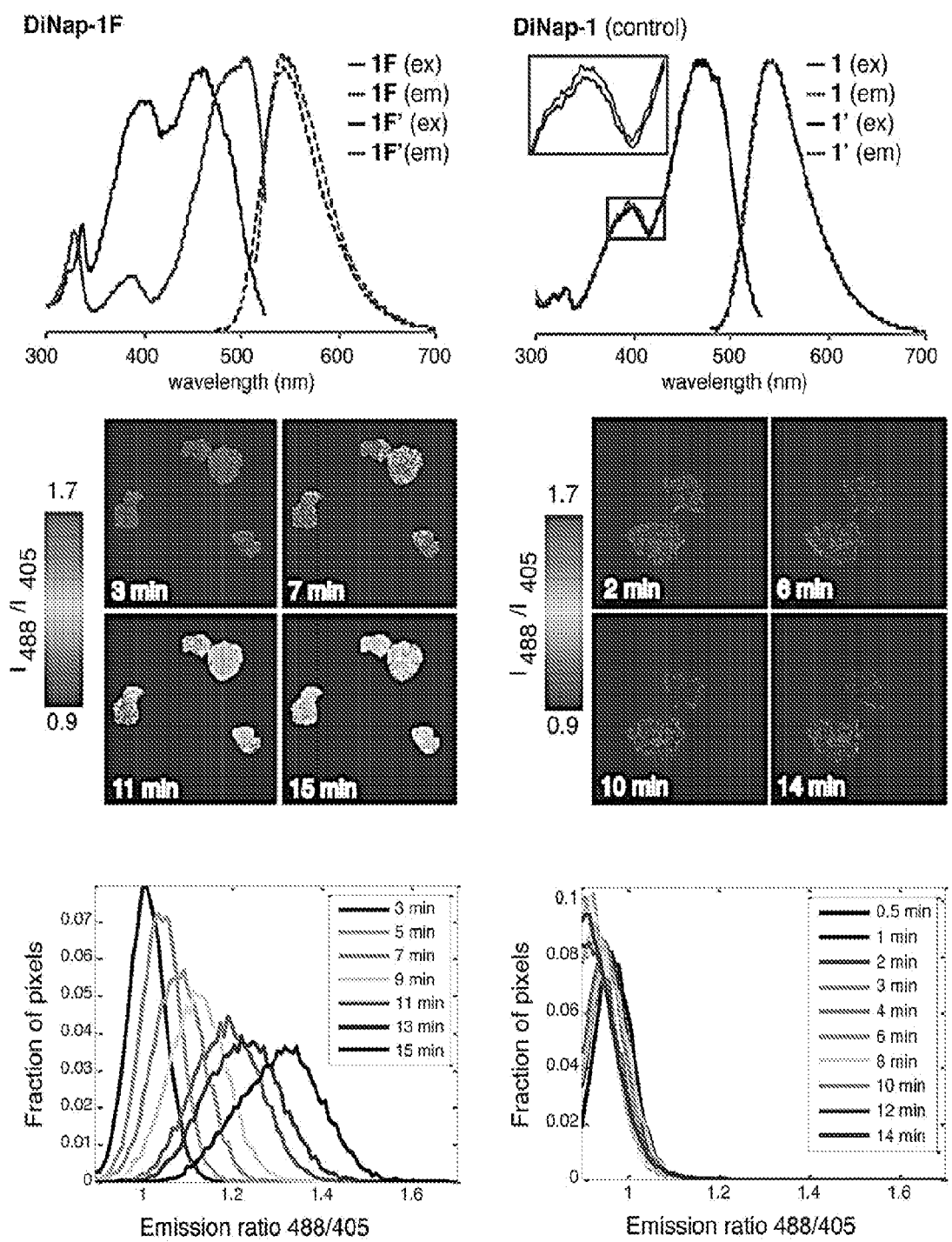
FIG. 5 shows gray-scaled spectroscopic properties of DiNap-AhpC C166S and TIRF microscopy B-cell hybridomas of DiNap-1F and DiNap-1.

Next, AhpC C166S labeled with either DiNap-1F or DiNap-1 was purified. FIG. 5 shows gray-scaled spectroscopic properties of DiNap-AhpC C166S and TIRF microscopy B-cell hybridomas of DiNap-1F and DiNap-1. After conjugation to DiNap-1F, there was a dramatic loss of the excitation peak at 400 nm. This is coupled with a significant excitation red-shifting of the primary excitation peak near 490 nm, providing an excellent excitation ratiometric fluorescent probe using the common 405 nm and 488 confocal lines (FIG. 5). In comparison, the control compound DiNap-1 exhibited exactly the same excitation and emission spectra, indicating that no chemical or electronic change occurs without the blocking group. Next, whether DiNap-1F could be used for ratiometric imaging sulfenylation in live cells by Total Internal Reflectance Fluorescence (TIRF) microscopy was tested. DiNap-1F, but not DiNap-1, clearly elicited a robust excitation ratio change over time. Overall, this data demonstrates that DiNap-1F is a sensitive ratiometric probe for imaging oxidation in live cells.

Figure 6:
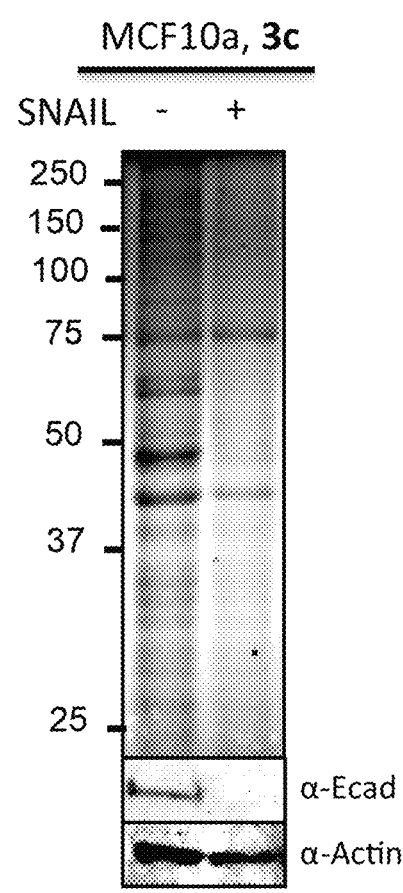
FIG. 6 shows the live-cell imaging of the present invention in MCF10a parent cell line or cell line overexpressing the transcription factor SNAIL.
Figure 6:
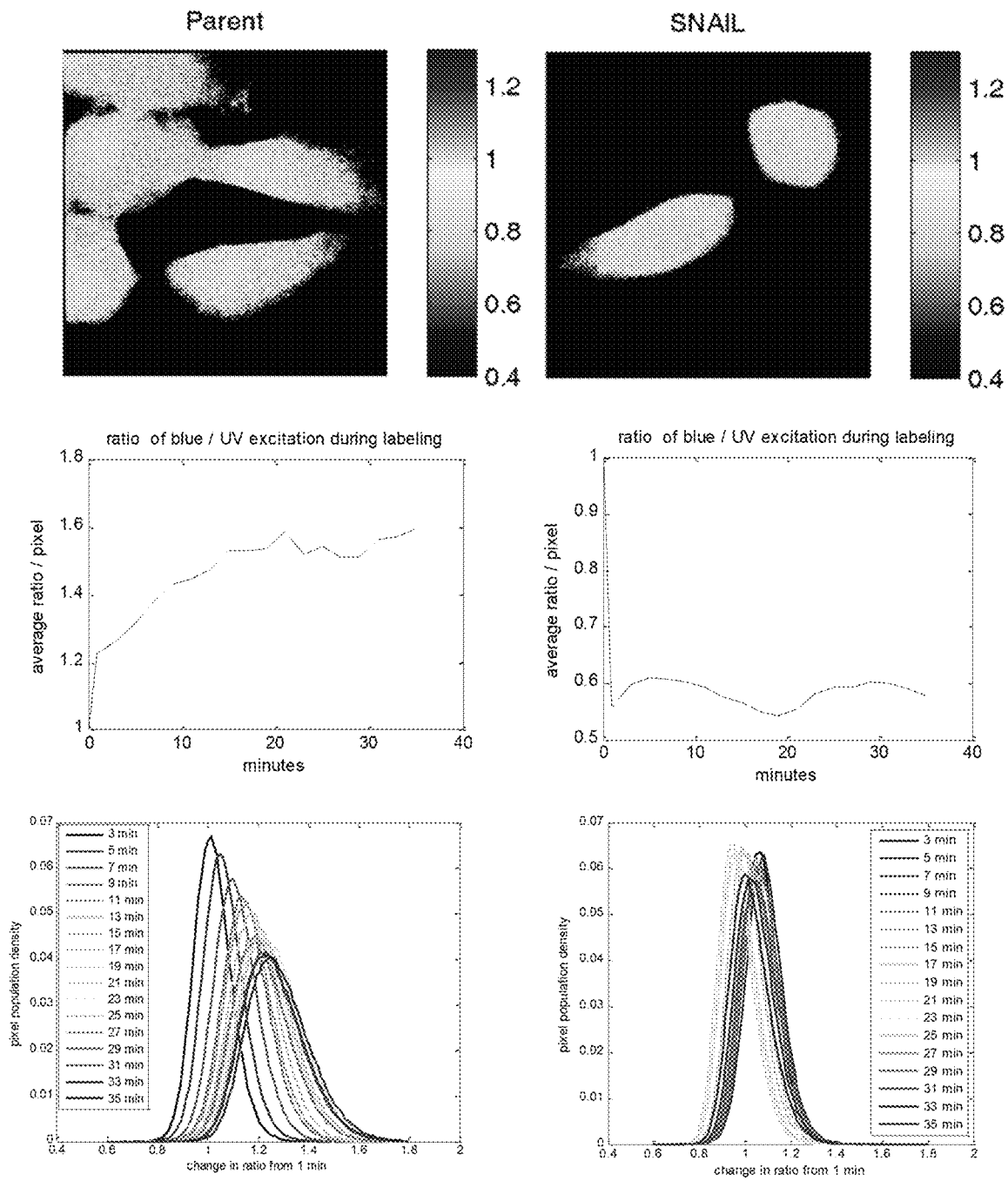

Upregulation or overexpression of SNAIL leads to epithelial to mesenchymal transition (EMT) and an increase in the malignancy of cancers. Proteomic data has shown that overexpression of SNAIL leads to an upregulation of antioxidant proteins. FIG. 6 shows the live-cell imaging of the present invention in MCF10a parent cell line or cell line overexpressing the transcription factor SNAIL.

Example II

Unlike visible light, radio waves and magnetic fields are easily transmitted through the body. $^{19}F$ has comparable receptivity (83%) and isotopic abundance (100.0%) to $^1H$ NMR, but unlike hydrogen it is virtually absent in biological samples, providing a high intrinsic signal-to-noise (see, e.g., Knight, J. C., et al., 2011 Rsc Advances 1, 1415-1425). It also has a wide chemical shift range (300 ppm) but changes chemical shift can be measured down to <1 ppm (see, e.g., Kitamura, N., et al., 2013 Bioorganic & Medicinal Chemistry Letters 23, 281-286). Thus, detection by $^{19}$F-NMR is highly sensitive to small chemical changes, which has been used to report biological activities or binding to cellular targets, in addition to biodistribution and pharmacokinetics. Recently, a mechanism-based small-molecule probe was developed to measure monoamine oxidase A activity, which undergoes oxidation and β-elimination of a fluorophenol to induce a 4.2 ppm $^{19}$F chemical shift (see, e.g., Yamaguchi, K. et al., 2011 Journal of the American Chemical Society 133, 14208-14211). Interestingly, α-fluoro-dimedone analogues are reported to display a measurable ppm chemical shift between the sp$^2$-hybridized (see, e.g., Saleur, D., et al., 2001 Journal of Organic Chemistry 66, 4543-4548) and the sp$^a$-hybridized thioether (see, e.g., Fuchigami, T., et al., 1995 Journal of Organic Chemistry 60, 3459-3464) conjugate (see, e.g., FIG. 9). Experiments conducted during the course of preparing embodiments for the present invention utilized this $^{19}$F-NMR shift in α-fluoro-AMCs as a platform towards quantitatively detecting in vivo sulfenylation. Most importantly, such embodiments utilize $^{19}$F-NMR to rapidly assay AMC scaffolds to select for enhanced sulfenylation reactivity. Experiments were developed to test if the described chemical switch could be applied for $^{19}$F NMR (FIG. 9). Initial experiments demonstrated F-DiNap-Morph resulted in a well-resolved chemical shift.

Figure 7:
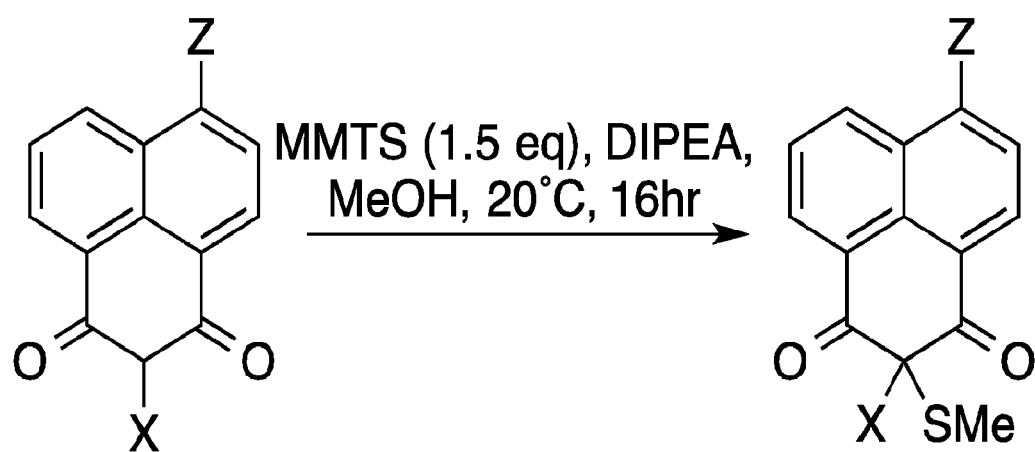
FIG. 7 shows a method to effectively sulfenylate active methylene compounds using thiosulfonates. Z in this case is any N- or O-containing pendant group. X is H, F, or Me.

FIG. 7 shows a method to effectively sulfenylate active methylene compounds using thiosulfonates. Methyl methane thiosulfonate (MMTS) is an activated disulfide compound and a stable sulfenylating agent. In organic solvents and with a mild base, the dye is monosulfenylated in modest yields.

Figure 8:
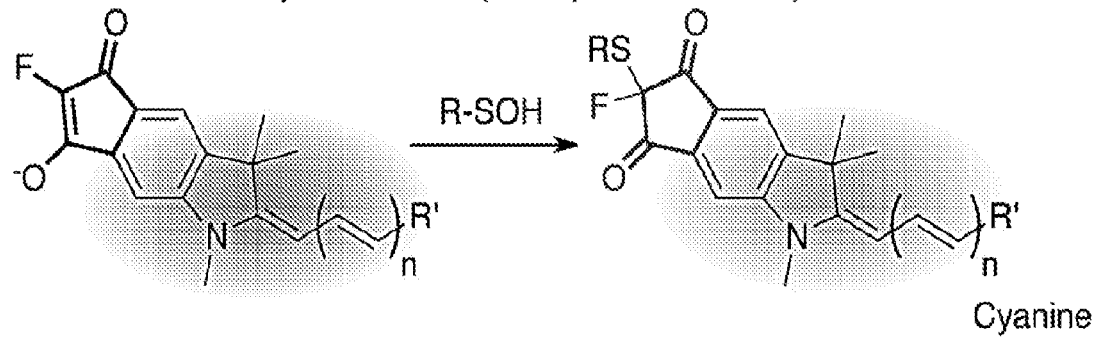
FIG. 8 shows additional ways to induce spectroscopic and fluorescence changes in dyes.
Figure 8:
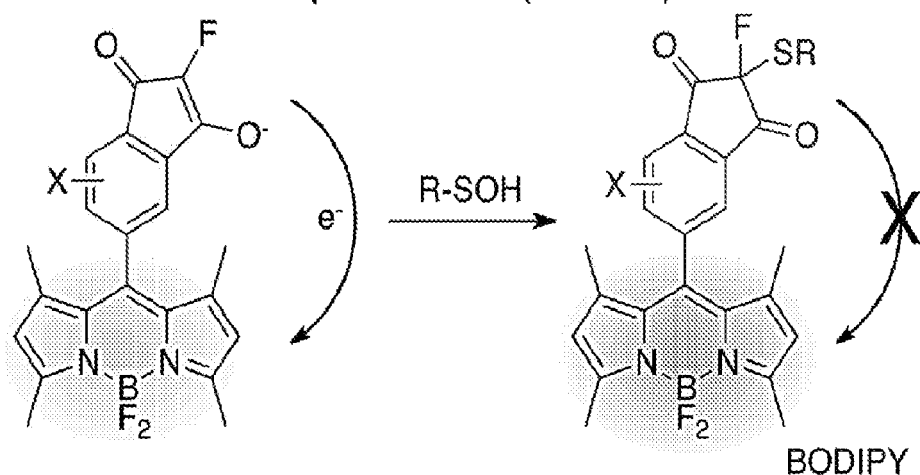
Figure 8:
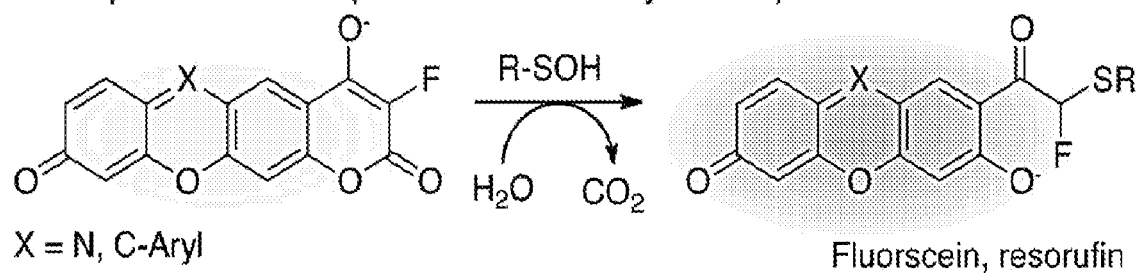

FIG. 8 shows additional techniques to induce spectroscopic and fluorescence changes in dyes.

Figure 10:
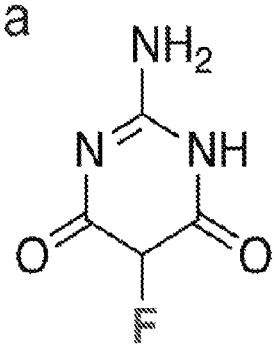
FIG. 10 Shows AMCs synthesized from A) diethyl fluoromalonate or B) fluoroacetoacetate.
Figure 10:
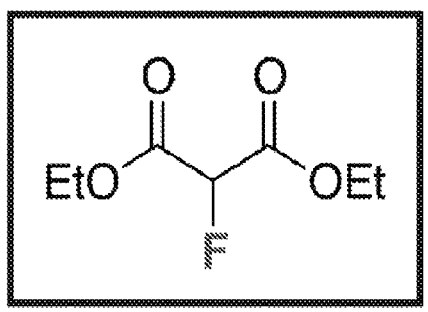
Figure 10:
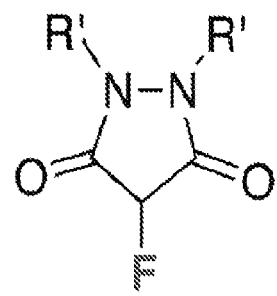
Figure 10:
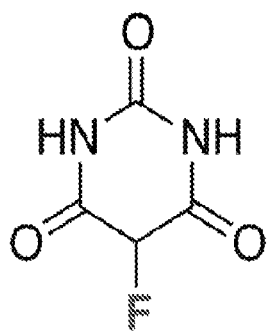
Figure 10:
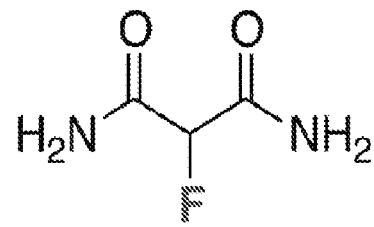
Figure 10:
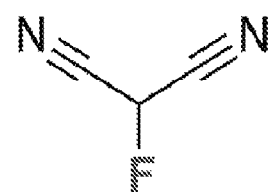
Figure 10:
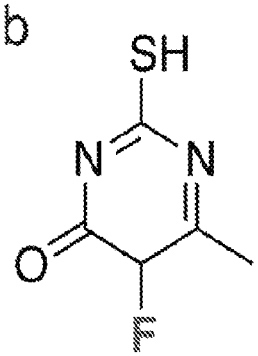
Figure 10:
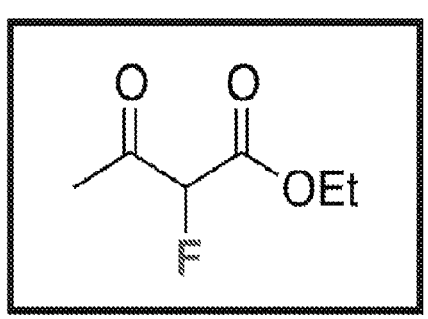
Figure 10:
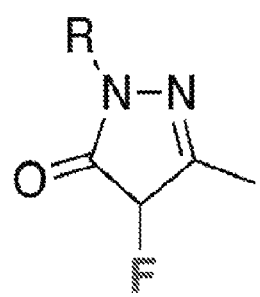
Figure 10:
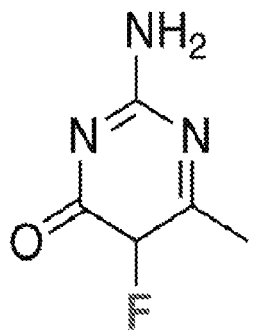
Figure 10:
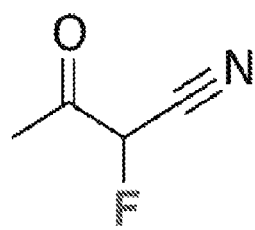
Figure 10:
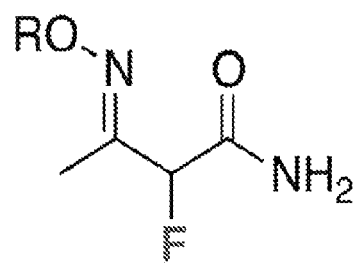

FIG. 10 Shows AMCs synthesized from a) diethyl fluoromalonate or b) fluoroacetoacetate.

Figure 12:
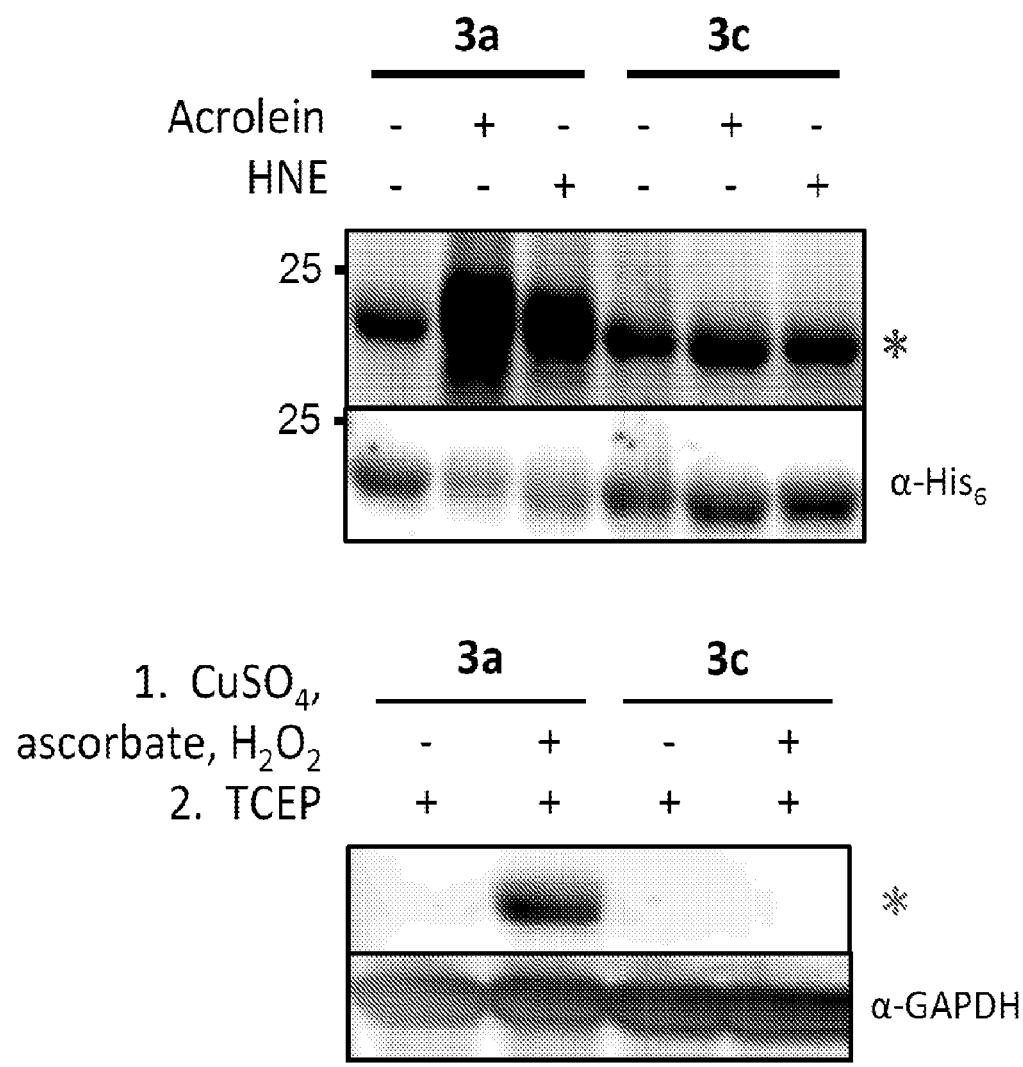
FIG. 12 shows the selectivity between substituted and non-substituted DiNaps carbonylated with enals acrolein and hydroxynonenal; and the selectivity over Fenton reaction conditions used to induce carbonylation.

FIG. 12 shows the selectivity between substituted and non-substituted DiNaps carbonylated with enals acrolein and hydroxynonenal; and the selectivity over Fenton reaction conditions used to induce carbonylation. Biological aldehydes are post-translation modifications known as carbonylation. Primary carbonylation involves the direct oxidation of Lys, Pro, Arg residues via the metal-catalyzed production of hydroxyl radicals from peroxide (Fenton conditions), while secondary carbonylation derives from the oxidation of polyunsaturated fatty acids by peroxide, producing unsaturated ene-als such as acrolein, or 4-hydroxynonenal which then conjugate to Cys, Lys, and His residues on proteins. Due to same input (peroxide) producing 1° and 2°, as well as sulfenylation, the present invention involves the first method to analyze sulfenic acid formation.

FIG. 13 shows HPLC elution traces of F-DiNap-Cl before and following exposure with pyridoxal. FIG. 14 shows HPLC elution traces of dimedone before and following exposure with pyridoxal. In these experiments, the incorporation of a blocking group inhibits other two-proton processes, such as the Knoevenagel condensation of AMCs with aldehydes. F-AMC analogues display a higher degree of selectivity. Due to the potential prevalence of various small-molecule and protein aldehydes in complex biological samples, it becomes important to be able to parse apart aldehyde and sulfenic acid formation.

Optimized $^{19}$F probes targeting sulfenylation were next designed. Though DiNap-1F exhibited all the hallmarks of a successful in vitro probe, the fluorescent aminonaphthalene scaffold is unnecessary for $^{19}$F NMR and the electron-rich aniline may present unfavorable pharmacokinetics in vivo. Therefore, a smaller α-fluoro dimedone probe specifically for $^{19}$F-NMR was synthesized. Other AMCs such as acetoacetate and 1,3-cyclopentanedione are known to react with sulfenic acids. However, these represent an extremely small sampling of potentially reactive AMCs. AMCs that can be readily synthesized from commercially available starting materials were generated, several of which are shown in FIG. 10. In addition to this initial library, a host of other synthetic routes are available using monofluorination reagents such as Selectfluor for monofluorination, and sequential perfluorination-monodefluorination. Using $^{19}$F chemical shift as a reporter of AMC conjugation, the reactivity of each probe for protein sulfenic acids and sulfonamides can be quickly assayed.

FIG. 9 shows experimentally determined shifts in 19F NMR signals between a) F-DiNaps bearing a morpholino pendant substituent and EtSF DiNap bearing a morpholino pendant substituent, b) F-DiNaps bearing a chloro substituent and EtSF DiNap bearing a chloro substituent, and c) F-DiNaps bearing an amino substituent and MeSF DiNap bearing an amino substituent on the rings.

FIG. 11a-c shows examples of ways the 19F NMR signal can be amplified.

Though $^{19}$F NMR is an attractive method, the transition from NMR tube to in vivo MRI imaging can suffer from low resolution and sensitivity. This can be overcome by special pulse sequences using resonators specifically tuned to $^{19}$F. This approach can be used to reach nominal resolutions of as low as 156 only 2-fold higher than the reported 78 μm by $^1$H MRI (see, e.g., Higuchi, M. et al., 2005 Nature Neuroscience 8, 527-533). The signal-to-noise can also be enhanced by using polyfluorinated probes to present a multiple similar or identical fluorine atoms (see, e.g., Schwarz, R., et al., 1999 Magnetic Resonance in Medicine 41, 80-86). In this approach, it is anticipated the output would not be a chemical shift observed from the α-proton. Instead, as with the fluorescent probes, conjugation could act as a chemical switch to trigger an environmental change sensed by the antennae fluorine nuclei (FIG. 11a). This gain in signal (3- to 18-fold) amplifies the effect of conjugation to improve detection (FIG. 11b). Additionally, MRI contrast agents often use paramagnetic metal proximal to the pulsed nuclei to decrease the overall relaxation time. This increases the number of scans that can be taken, and increases the overall contrast and resolution of the image. Cell-permeable gadolinium contrast agents have been demonstrated (see, e.g., Yamane, T. et al., 2011 Bioconjugate Chemistry 22, 2227-2236), as well as less-common manganese-porphyrins (FIG. 11c) (see, e.g., Lee, T. et al., 2010 Chemistry & Biology 17, 665-673).

FIG. 11d shows expected small animal MRI visualization of in vivo sulfenylation.

Experiments will be conducted utilizing $^{19}$F-NMR AMC probes to study the role of DJ-1 in suppressing cysteine sulfenylation. DJ-1 knockout cells, bacteria and yeast deletion strains of peroxiredoxins, DJ-1/PARK7, and other redox chaperones implicated in suppressing protein sulfenylation will be utilized. Such intact organisms will be used to monitor the in vivo rate of AMC conjugation. Furthermore, oxidants, reductants, or antioxidants will be added to monitor the impact on protein sulfenylation. Similar experiments will then be translated to mammalian cells, particularly the DJ-1/PARK knockout cells mentioned above.

Example III

The probes of the present invention will be tested using a similar series of biochemical assays to define reactivity and cell permeability. In addition, the response of such probes to peroxide addition in live cells will be tested. In addition, the spatial profile of sulfenylation of cancer cells (including, for example, A431 cells shown to couple EGF stimulation to Nox activation and EGFR sulfenylation (see, e.g., Paulsen, C. E. et al., 2012 Nature Chemical Biology 8, 57-64)) will be tested.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

We claim:

1. A method for detecting protein sulfenylation within cysteine residues of a protein or a thiol-containing metabolite, comprising:
   providing a biological sample comprising one or more proteins having cysteine residues and/or biological metabolites having a thiol and a composition comprising a fluorine labeled active methylene compound (AMC) wherein a single α-proton is replaced by the fluorine providing a sulfenylation reactive probe;
   exposing the composition to the biological sample such that an interaction between the probe and a sulfenic acid side chain of a cysteine residue or other thiol results in a stable irreversible thioether linkage of the probe with the sulfenic acid side chain,
   measuring the spectroscopic properties of the probe following exposure of the composition to the biological sample, wherein and
   characterizing the cysteine residues of the protein as having under gone sulfenylation if the measuring indicates an altered spectroscopic property of the sulfenylation reactive probe via the stable thioether linkage to the sulfenic acid, wherein the sulfenylation reactive probe is selected from

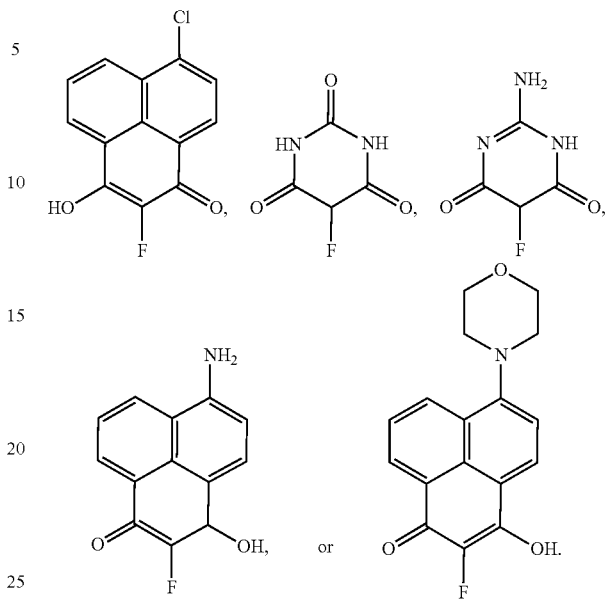

2. The method of claim 1, further comprising identifying the protein having been characterized as having undergone sulfenylation and/or identifying the exact amino acid sites on the protein having been characterized as having undergone sulfenylation.

3. The method of claim 1, wherein the spectroscopic properties are measured with ratiometric fluorescence imaging.

4. The method of claim 1, wherein the spectroscopic properties are measured with $^{19}$F-NMR/MRI.

5. The method of claim 1, wherein the spectroscopic properties are measured with mass spectrometer.

6. The method of claim 1, wherein the biological sample is an ex vivo sample obtained from a living subject.

7. The method of claim 1, wherein the biological sample is an in vitro biological sample.

8. The method of claim 1, wherein the biological sample is a living mammalian subject.

9. The method of claim 8, wherein the living mammalian subject is a living mouse.

10. The method of claim 2, wherein the living mammalian subject is a living human being.

11. The method of claim 2, wherein mass spectrometry is used to characterize the cysteine residues of the protein characterized as having undergone protein sulfenylation.

12. The method of claim 1, wherein the biological sample is a mammalian biological sample.

13. The method of claim 1, wherein the biological sample is a human biological sample.

14. The method of claim 1, wherein the sulfenylation reactive probe is a fluorine substituted dimedone.

15. The method of claim 1, wherein the fluorine is isotope $^{19}$F.

* * * * *